US006089108A

United States Patent [19]
Lucas

[11] Patent Number: 6,089,108
[45] Date of Patent: *Jul. 18, 2000

[54] HOT BOTTLE INSPECTION APPARATUS AND METHOD

[75] Inventor: Philip J. Lucas, Lakewood, Colo.

[73] Assignee: Coors Brewing Company, Golden, Colo.

[ * ] Notice: This patent is subject to a terminal disclaimer.

[21] Appl. No.: 08/914,984

[22] Filed: Aug. 20, 1997

Related U.S. Application Data

[63] Continuation-in-part of application No. 08/509,049, Jul. 31, 1995, Pat. No. 5,734,467, and application No. 08/526,897, Sep. 12, 1995.

[51] Int. Cl.[7] .......................... G01N 21/15; G01N 21/90; G01M 19/00
[52] U.S. Cl. ................. 73/865.8; 250/223 B; 250/227.2; 356/239.4; 382/142
[58] Field of Search ................................ 73/865.8, 865.9, 73/866.5; 250/223 B, 227.2; 382/141, 142; 356/239.4, 240.1

[56] References Cited

U.S. PATENT DOCUMENTS

| | | |
|---|---|---|
| 3,387,551 | 6/1968 | Hughes . |
| 3,708,679 | 1/1973 | Stock et al. ........................ 250/223 R |
| 3,767,374 | 10/1973 | Iacovazzi et al. ....................... 65/165 |
| 3,886,356 | 5/1975 | Gomm et al. ........................... 250/223 |
| 4,004,904 | 1/1977 | Fergusson ................................ 65/158 |
| 4,019,819 | 4/1977 | Lodzinski .................................. 356/73 |
| 4,026,656 | 5/1977 | Kusz et al. ................................ 356/51 |
| 4,306,835 | 12/1981 | Hurley .................................... 415/118 |
| 4,332,606 | 6/1982 | Gardner .................................... 65/158 |
| 4,402,721 | 9/1983 | Ericson et al. ............................. 65/29 |
| 4,414,566 | 11/1983 | Peyton et al. ................... 250/223 B X |
| 4,431,436 | 2/1984 | Lulejian .................................... 65/159 |
| 4,492,476 | 1/1985 | Miyazawa ............................... 356/428 |
| 4,494,656 | 1/1985 | Shay et al. .............................. 209/524 |
| 4,500,203 | 2/1985 | Bieringer ................................ 356/240 |
| 4,553,217 | 11/1985 | Daudt et al. ............................ 364/560 |
| 4,599,099 | 7/1986 | Jones ........................................ 65/29 |
| 4,606,746 | 8/1986 | Keller ....................................... 65/29 |
| 4,608,072 | 8/1986 | Fenton ...................................... 65/79 |
| 4,614,531 | 9/1986 | Bishop et al. ............................ 65/158 |

(List continued on next page.)

FOREIGN PATENT DOCUMENTS

| | | |
|---|---|---|
| 2 094 530 | 9/1982 | United Kingdom . |
| 2 179 648 | 3/1987 | United Kingdom . |
| 4887 | 2/1997 | WIPO . |

OTHER PUBLICATIONS

Abstract of WO98/07018 dated Feb. 19, 1998 by Hidalgo et al "Method for Measurement of Light Transmittance".

"The Hand Book of Glass Manufacture" vol. II, Fay V. Tooley, published by Books for Industry, Inc. and the Glass Industry Magazine Division of Magazines for Industry, Inc. 1974 month not given, Library of Congress No. 74–77520, PPS 961–975.

*Primary Examiner*—Thomas P. Noland
*Attorney, Agent, or Firm*—Klaas, Law, O'Meara & Malkin, P.C.; William P. O'Meara, Esq.; Michael A. Goodwin, Esq.

[57] ABSTRACT

A bottle inspection apparatus and method are disclosed in which an improved housing contains an imaging device which is focused at a target area through an unobstructed window opening formed in a wall of the housing. The housing includes a sleeve member which may be attached to the housing in the vicinity of the unobstructed window opening and which may be positioned in close proximity to the imaging device, thus creating a restricted air path between the sleeve member and the imaging device which restricts the flow of cooling air exiting the housing. The imaging device may be mounted on a slide mount system such that it is adjustably moveable toward and away from the sleeve in order to adjustably control the amount of air restriction imposed and, thus, adjustably control the rate at which cooling air exits the housing.

20 Claims, 11 Drawing Sheets

U.S. PATENT DOCUMENTS

| | | | |
|---|---|---|---|
| 4,639,263 | 1/1987 | Kulikauskas | 65/158 |
| 4,649,503 | 3/1987 | Keller | 364/552 |
| 4,664,521 | 5/1987 | Scott et al. | 356/240 |
| 4,675,042 | 6/1987 | Taddei-Contreras et al. | 65/158 |
| 4,679,075 | 7/1987 | Williams et al. | 358/106 |
| 4,691,830 | 9/1987 | Ahl et al. | 209/523 |
| 4,694,158 | 9/1987 | Leser | 250/223 B |
| 4,762,544 | 8/1988 | Davey | 65/29 |
| 4,842,411 | 6/1989 | Wood | 356/376 |
| 4,915,237 | 4/1990 | Chang et al. | 209/524 |
| 4,948,956 | 8/1990 | Fukuchi | 250/223 |
| 4,997,769 | 3/1991 | Lundsgaard | 436/66 |
| 5,187,368 | 2/1993 | Galante et al. | 250/341 |
| 5,305,081 | 4/1994 | Gooch et al. | 356/240 |
| 5,345,309 | 9/1994 | Wertz et al. | 356/372 |
| 5,354,984 | 10/1994 | Baldwin | 250/223 B |
| 5,369,713 | 11/1994 | Schwartz et al. | 356/240.1 X |
| 5,414,777 | 5/1995 | van der Schaar et al. | 382/142 |
| 5,437,702 | 8/1995 | Burns et al. | 65/29.12 |
| 5,510,610 | 4/1996 | Baldwin | 250/223 B |
| 5,510,621 | 4/1996 | Goldman | 250/343 |
| 5,592,286 | 1/1997 | Fedor | 250/223 B X |
| 5,717,486 | 2/1998 | Burri et al. | 250/223 B |
| 5,734,467 | 3/1998 | Lucas | 356/240 |
| 5,935,285 | 8/1999 | Lucas | 356/239.4 X |

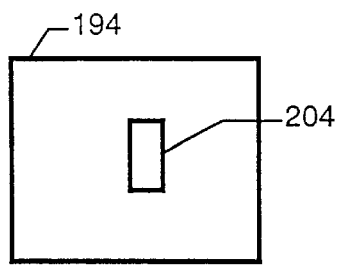 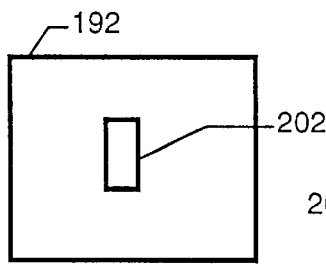 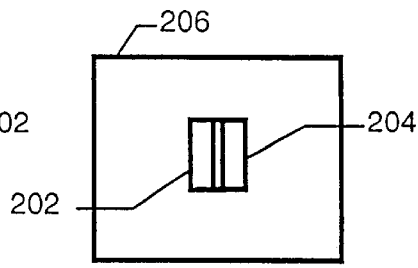
*FIG. 9A*  *FIG. 9B*  *FIG. 9C*
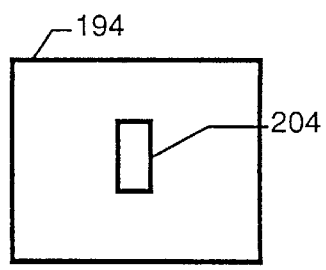 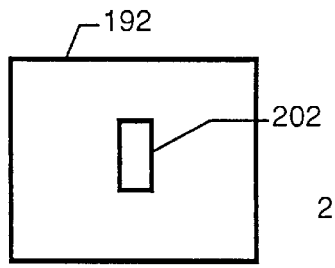 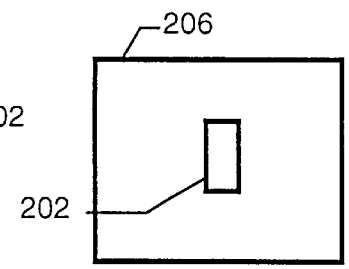
*FIG. 10A*  *FIG. 10B*  *FIG. 10C*
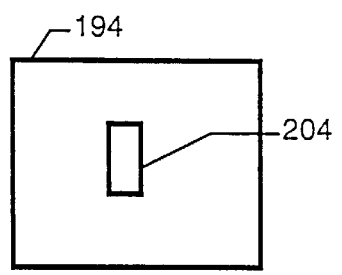 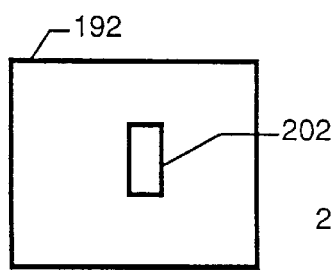 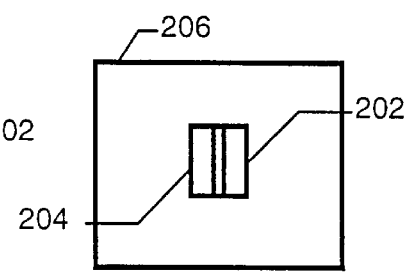
*FIG. 11A*  *FIG. 11B*  *FIG. 11C*

HOT BOTTLE INSPECTION APPARATUS AND METHOD

This is a continuation-in-part of application Ser. No. 08/509,049, filed Jul. 31, 1995 and now U.S. Pat. No. 5,734,467 and of application Ser. No. 08/526,897 filed Sep. 12, 1995.

FIELD OF THE INVENTION

The present invention relates generally to glass bottle production and, more particularly, to a glass bottle inspection apparatus adapted for use at the hot end of a glass bottle production line.

BACKGROUND OF THE INVENTION

The manufacture of glass bottles begins with the preparation of raw materials. Sand and soda ash are measured in precise quantities, mixed together and conveyed to storage silos located over large melting furnaces. The mixed materials are continuously metered into the furnaces to replace molten glass which is dispensed from the furnaces after melting.

The furnaces are heated by a combination of natural gas and electricity and are operated at a temperature of over 2500 degrees Fahrenheit. The melted mixture of raw materials forms molten glass which flows from the furnaces through refractory channels, also known as forehearths, to a position over bottle forming machines.

A bottle forming machine known in the industry as an "I.S. machine" draws the glass into individual gobs and drops each gob into a blank mold. The blank mold forms a bottle preform, also referred to as a parison. The preform is transferred to a blow mold where it is blown by compressed air into a bottle. Each blow mold cavity typically contains indicia provided on a bottom wall thereof which embosses each bottle with code characters indicating the mold cavity in which it was formed.

The molds are lubricated by oil-borne carbon. The hot mold vaporizes the oil and some of the carbon immediately upon contact, leaving most of the carbon deposited upon the mold. Thus, the area around the mold is an extremely dirty environment filled with oil and carbon vapors and condensate.

An I.S. machine typically has between six and sixteen individual sections, with each section having from one to four blow mold cavities. Each section may be capable of manufacturing one to four bottles at a time. A typical eight section, triple gob, I.S. machine used in the production of beer bottles may produce 270 beer bottles per minute.

After the bottles have been blown, they are transferred from the respective blow mold cavities onto a moving conveyor belt. The bottles are positioned on the moving conveyor belt in a single line in a sequence corresponding to the sequence of the blow mold cavities in which the bottles were formed. The finished bottles transferred onto the conveyor from the blow mold are still red hot (approximately 1,000 degrees Fahrenheit). These hot bottles are conveyed by the conveyor belt through a hot end coating hood where they are chemically treated with a stannous chloride compound for strengthening. Vapors from the hot end coating hood also contribute significantly to the harsh environment found at the "hot end" of the bottle production line.

After passing through the hot end coating hood, the hot bottles are conveyed through an annealing oven or lehr where they are reheated and then cooled in a controlled manner to eliminate stresses in the glass. This annealing process typically takes from 20 to 30 minutes. The annealing process is the last process which takes place at the hot end of the production line. The portion of the production line downstream from the annealing oven is referred to as the "cold end" of the production line. In contrast to the hot end, the cold end is neither hot nor dirty. At the cold end of the production line, bottles are conveyed through a series of inspection devices. Typical prior art inspection devices include a squeezer which physically squeezes each bottle to check its sidewall strength. Another prior art cold end inspection device is referred to in the industry as a total inspection machine or T.I.M. which is sold by Emhart Glass having a business address of 123 Day Hill Road, Windsor, Conn. 06095. The total inspection machine physically engages each bottle and checks the size of the bottle neck opening and the thickness of the bottle sidewall and reads the code on the bottle bottom wall to determine the mold of origin. On a statistical sampling basis, the T.I.M. also sends bottles off line to be tested for burst strength, weighing, and measuring. Reports generated from the T.I.M. correlate bottle defects with the mold of origin. Another typical prior art inspection device is known as a "super scanner" sold by Inex, 13327 U.S. 19 North, Clearwater, Fla. 34624. The super scanner operates on each bottle on line. It initially scans a bottle, then engages and rotates the bottle approximately 90 degrees and scans it again. The super scanner uses image analysis to perform certain dimensional parameter checks of the bottle.

At both the T.I.M. and the super scanner inspection stations, defective bottles may be rejected by a cold end rejection device. After passing through the cold end inspection stations, bottles are transferred to a case packer machine, placed into a cardboard carton and conveyed to a palletizer machine for being placed in pallets. Loaded pallets are then shipped to a filling facility, such as a brewery.

A problem experienced with traditional glass bottle manufacturing operations as described above results from the fact that the bottle inspection stations are located at the cold end of the bottle production line. If a particular blow mold cavity begins producing defective bottles, e.g. as a result of a foreign object in the mold, the first defective bottle produced will not be detected until 30 to 40 minutes after its formation in the blow mold. As a result of this detection delay, the defective mold cavity will have continued to produce hundreds of defective bottles during the period between the first defective production and discovery of the first defective bottle. Furthermore, unless the defect is a defect of the type discovered by the T.I.M. machine which also identifies each bottle with a blow mold, the mold causing the problem will not be immediately apparent to the operator. As a result, the production operation must be shut down and each of the mold cavities of the I.S. machine must be inspected to detect the origin of the problem. Such shut down and inspection may be very time consuming and results in significant production loss in addition to the scrap produced by the defective mold cavity. Locating an inspection machine at the hot end of the bottle production line is difficult for a number of reasons: (1) as a result of the elevated temperature of the bottles at the hot end of the line, any engagement of the bottles by an inspection machine as is conventional with cold end inspectors would result in deformation of the bottle surface producing an ascetically unacceptable bottle; (2) the heat of the bottles at the hot end causes the bottles to glow and would thus make reading of mold origin indicating characters on the base of the bottle extremely difficult or impossible; (3) the contaminants in the atmosphere at the hot end of the line tend to coat the surface of any optical device used to image the bottles rendering imaging difficult or impossible; (4) the extreme heat and contamination at the hot end of the line is damaging to any electronics used on inspection devices positioned at the hot end.

A solution to these problems is addressed in U.S. Pat. No. 5,437,702 issued Feb. 27, 1995 to Burns et al. for HOT BOTTLE INSPECTION APPARATUS AND METHOD, which is hereby specifically incorporated by reference for all that is disclosed therein. The Burns et al. patent discloses a non-contacting optical imaging inspection system that is located at the hot end of a bottle line. The optics and electronics employed are shielded from the harsh environment at the hot end of the production line by a fluid cooled housing. Clear panels in one of the housing walls enable the imaging devices within the housing to image passing bottles without the optics thereof being exposed to the harsh environment of the hot end. Fluid jets are provided adjacent to these clear panels in order to prevent contaminants from building up on the outer surface of the panels. Monitoring signals from the I.S. machine and the bottle conveyor are processed by data processing apparatus to determine the mold of origin of each bottle which is being imaged, thus obviating the need to read indicia on the surface of a glowing bottle. The image data from each bottle is analyzed to determine whether or not the bottle is defective.

Although this machine generally works well, it has been found that the clear panels of the fluid cooled housing still occasionally become dirtied, requiring maintenance and/or resulting in degradation of performance.

A solution to these problems associated with clear panels has been addressed in U.S. patent application Ser. No. 08/526,897 of Lucas for HOT BOTTLE INSPECTION APPARATUS AND METHOD, filed Sep. 12, 1995, which is hereby specifically incorporated by reference for all that is disclosed therein.

The Lucas application discloses fluid cooled housings in which the clear panels discussed above have been replaced with unobstructed openings which allow pressurized cooling fluid contained in the fluid cooled housing to escape therethrough. Although this arrangement effectively eliminates the problems associated with dirty panels discussed above, it has been found that the unobstructed openings generally allow cooling air to escape the housing at too great a rate, thus making it difficult to maintain positive pressure within the housing. It has further been found that eddy currents sometimes form around the edges of the unobstructed openings, causing contaminated air from the exterior of the housing to be drawn into the housing.

SUMMARY OF THE INVENTION

The present invention is directed to an improved housing for imaging devices and associated electronics. An imaging device within the housing may be focused at a target area through an unobstructed window opening formed in a wall of the housing. The housing includes a sleeve member which may be attached to the housing in the vicinity the unobstructed window opening. The sleeve member is positioned in close proximity to the imaging device contained within the housing, thus creating a restricted air path between the sleeve member and the imaging device which restricts the flow of cooling air exiting the housing. The imaging device may be mounted on a slide mount system such that it is adjustably moveable toward and away from the sleeve. In this manner, the air restriction formed between the sleeve and the imaging device may be varied in order to adjustably control the amount of air restriction imposed and, thus, adjustably control the rate at which cooling air exits the housing.

The present invention is also directed to a laser triggering system in which the laser trigger device is mounted in a location such that the laser beam generated by the laser triggering system intersects the target area at a steep angle. This arrangement prevents interference with the laser beam by human operators who, from time to time, may be located near the target area.

The present invention is also directed to the use of an electronically shuttered imaging device and an associated light source. The light source may be a conventional AC powered halogen light source which is operated at a wattage lower than its rated wattage in order to prevent the detrimental effects of AC induced light fluctuations.

BRIEF DESCRIPTION OF THE DRAWING

An illustrative and presently preferred embodiment of the invention is shown in the accompanying drawing in which:

FIGS. 9A–9C schematically illustrate a bottle image from a first imaging device, a bottle image from a second imaging device and a combined bottle image, respectively, when the bottle being imaged is transversely misaligned closer to the imaging devices.

FIGS. 10A–10C schematically illustrate a bottle image from a first imaging device, a bottle image from a second imaging device and a combined bottle image, respectively, when the bottle being imaged is transversely aligned.

FIGS. 11A–11C schematically illustrate a bottle image from a first imaging device, a bottle image from a second imaging device and a combined bottle image, respectively, when the bottle being imaged is transversely misaligned further from the imaging devices.

DETAILED DESCRIPTION OF THE INVENTION

Figure 1:
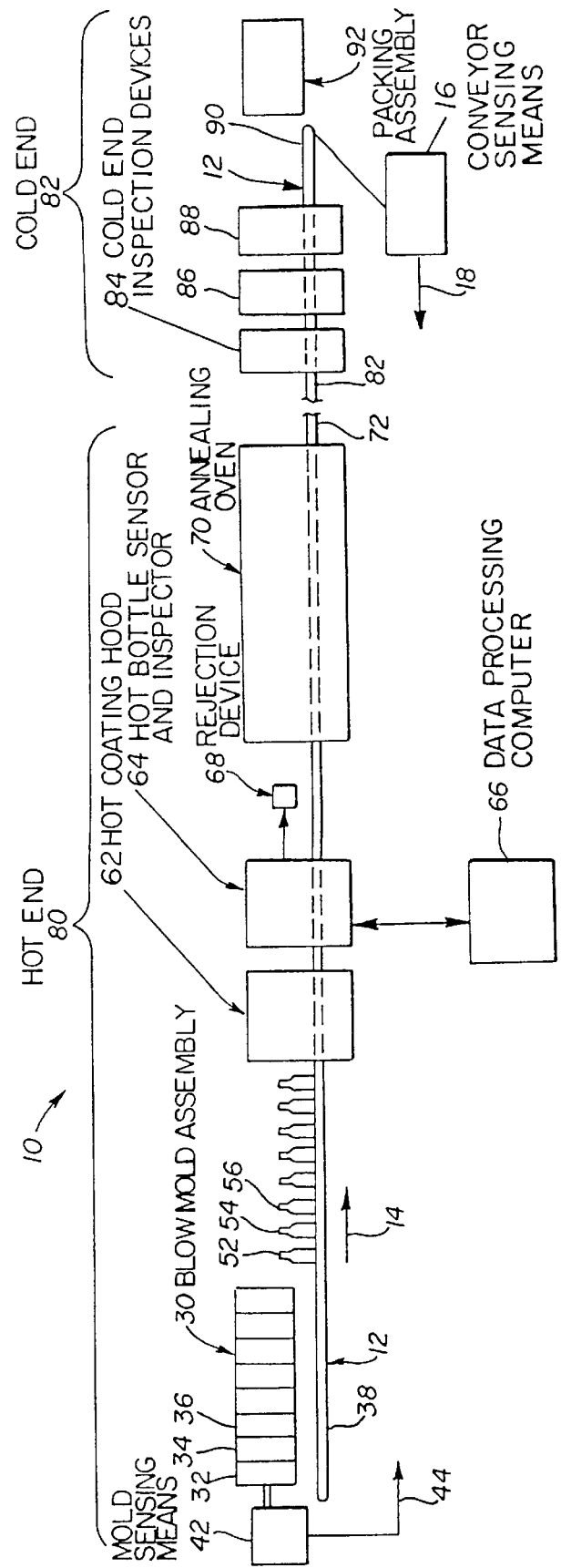
FIG. 1 is a schematic diagram of a glass bottle production line.

In general, the invention may pertain to an apparatus 64 for measuring at least one unknown characteristic of objects 52, 54, 56 being conveyed along an object pathway on a conveyor 12. The apparatus includes an enclosure 350 located adjacent the conveyor 12. The enclosure 12 has an enclosure interior located within the enclosure 350 and an enclosure exterior located outside of the enclosure 350. The enclosure 350 also has an opening 372 which extends between the enclosure exterior and the enclosure interior and a sleeve member 390 having a first end 398 and a second end 400. The sleeve member first end 398 is located proximate the enclosure opening 372. An image generating device 104 is located in the enclosure interior and aimed through the sleeve member 390 at a location 50 within the object pathway. The sleeve member second end 400 is located proximate the image generating device 104.

The invention may also include a method of measuring at least one unknown characteristic of objects 52, 54, 56 being conveyed along an object pathway on a conveyor 12. The method includes the steps of providing an enclosure assembly 350 located adjacent the conveyor 12 which includes an enclosure assembly interior located within the enclosure assembly 350 and an enclosure assembly exterior located outside of the enclosure assembly 350; pressurizing the enclosure assembly interior to a pressure higher than that of the enclosure assembly exterior; providing a passageway 396 extending between the enclosure assembly exterior and the enclosure assembly interior; providing a flow of air 502, 504 from the enclosure assembly interior to the enclosure assembly exterior through the passageway 396; providing an image generating device 104 in the enclosure assembly interior; aiming the image generating device 104 through the passageway 396 at a location 50 within the object pathway; and restricting the flow of air through the passageway 396 by locating the image generating device 104 in proximity to a portion 390 of the enclosure assembly adjacent the passageway 396.

The invention may also pertain to an apparatus 64 for measuring at least one unknown characteristic of objects 52, 54, 56 being conveyed along an object pathway on a conveyor 12. The apparatus 64 includes a first enclosure 300 located adjacent the conveyor 12 and a second enclosure 350 located adjacent the conveyor 12. Each of the first and second enclosures 300, 350 include: an enclosure interior located within the enclosure 300, 350 and an enclosure exterior located outside of the enclosure 300, 350; an opening 372 in the enclosure, the opening 372 extending between the enclosure exterior and the enclosure interior; a sleeve member 390 having a first end 398 and a second end 400, the sleeve member first end 398 located proximate the enclosure opening 372; an image generating device 104 located in the enclosure interior and aimed through the sleeve member 390 at a location 50 within the object pathway; and the sleeve member second end 400 located proximate the image generating device 104.

The invention may also pertain to an apparatus for imaging objects 52, 54, 56 being conveyed along an object pathway located on a conveyor 12. The apparatus may include a substantially planar conveyor upper surface 13, FIG. 16, located on the conveyor 12 and upon which the objects 52, 54, 56 are supported while being conveyed along the object pathway; at least one image acquisition device 102, 104 located adjacent the conveyor 12 and aimed at a location within the object pathway; and a laser triggering system including a laser emitting device 510, a laser reflecting device 514 and a laser sensing device 510. The plane of the substantially planar conveyor upper surface 13 defines a first space located on one side of the plane and a second space located on the opposite side of the plane from the first space. The laser emitting device 510 is located in the first space and the laser reflecting device 514 is located in the second space.

Having thus described the method and apparatus for measuring unknown characteristics of an object in general, further features thereof will now be specifically described.

FIG. 1 is a schematic illustration of a glass bottle production line 10. The production line comprises a conveyor 12 which defines a bottle conveyance path. The conveyor moves bottles downstream in direction 14. A conveyor monitor assembly 16 which may be, for example, a conventional electronic encoder mounted on a conveyor motor shaft, monitors the conveying movement of conveyor 12 and produces a conveyor displacement signal 18 representative thereof. In most bottle production lines the conveyor 12 is mechanically linked to the drive mechanism of the blow mold such that conveyor speed is always directly proportional to the speed of operation of the blow mold. In such a case any device which monitors mold displacement, for example, an incremental encoder mounted on the shaft of the mold drive unit, would also indicate conveyor displacement and is to be considered a conveyor monitor.

A blow mold assembly 30 comprises a plurality of mold cavity portions 32, 34, 36, etc. The blow mold assembly 30 may comprise a portion of a conventional I.S. machine. The blow mold assembly 30 is positioned at an upstream end 38 of conveyor 12. A mold monitor assembly 42 generates a mold transfer signal 44 each time the blow mold 30 transfers bottles onto conveyor 12. Bottles 52, 54, 56, etc. are produced by mold cavity portions 32, 34, 36, etc. and are transferred to conveyor 12 in single file in a sequence corresponding to the sequence of their respective blow mold cavities of origin. The bottles 52, 54, 56 may be formed with indicia thereon indicative of the blow mold cavity of origin. The bottles 52, 54, 56, etc. are transferred onto the conveyor 12 at an elevated temperature which may be approximately 1000 degrees Fahrenheit such that the bottles are glowing.

A hot coating hood 62 is positioned at a station along the conveyor 12 a short distance downstream, e.g. 10 feet, from the blow mold 30.

A hot bottle inspection apparatus, also referred to herein as a hot bottle inspector 64, is positioned at a fixed station along the conveyor which may be a short distance, e.g. two feet, downstream from the hot coating hood 62. The hot bottle inspector 64 may thus be located in an extremely hot and dirty environment at the hot end 80 of the production line. A remote computer 66 removed from the harsh environment at the hot end of the production line is operably connected to the hot bottle inspector 64 and is accessible to a production line operator. A rejection device 68 may be positioned immediately downstream from the hot bottle inspector 64 and is operable to remove bottles from the conveyor in response to commands from the hot bottle inspector 64.

An annealing oven 70 of a conventional type may be positioned downstream of the rejection device 68 and defines, at its downstream end portion 72, the terminal end portion of the "hot end" 80 of the bottle production line 10. In a typical production line used for producing glass beer bottles, the period of time elapsing from the transfer of a bottle onto the conveyor 12 by the blow mold 30 to the exit of that bottle from the downstream end 72 of annealing oven 70 may be thirty minutes.

The portion of the production line 10 located downstream of the annealing oven exit 72 constitutes the "cold end" 82 of the production line. The cold end of the production line may comprise conventional cold end inspection devices 84, 86, 88 such as a squeezer, a T.I.M. machine, and a super inspector machine such as previously described in the "Background of the Invention" section of this application. The first of these cold end inspectors 84 may be positioned, e.g. 100 feet, downstream from the exit 72 of annealing oven 70. A conventional packing assembly 92, such as described above, may be provided downstream from the cold end inspection devices 84, 86, 88.

Figure 2:
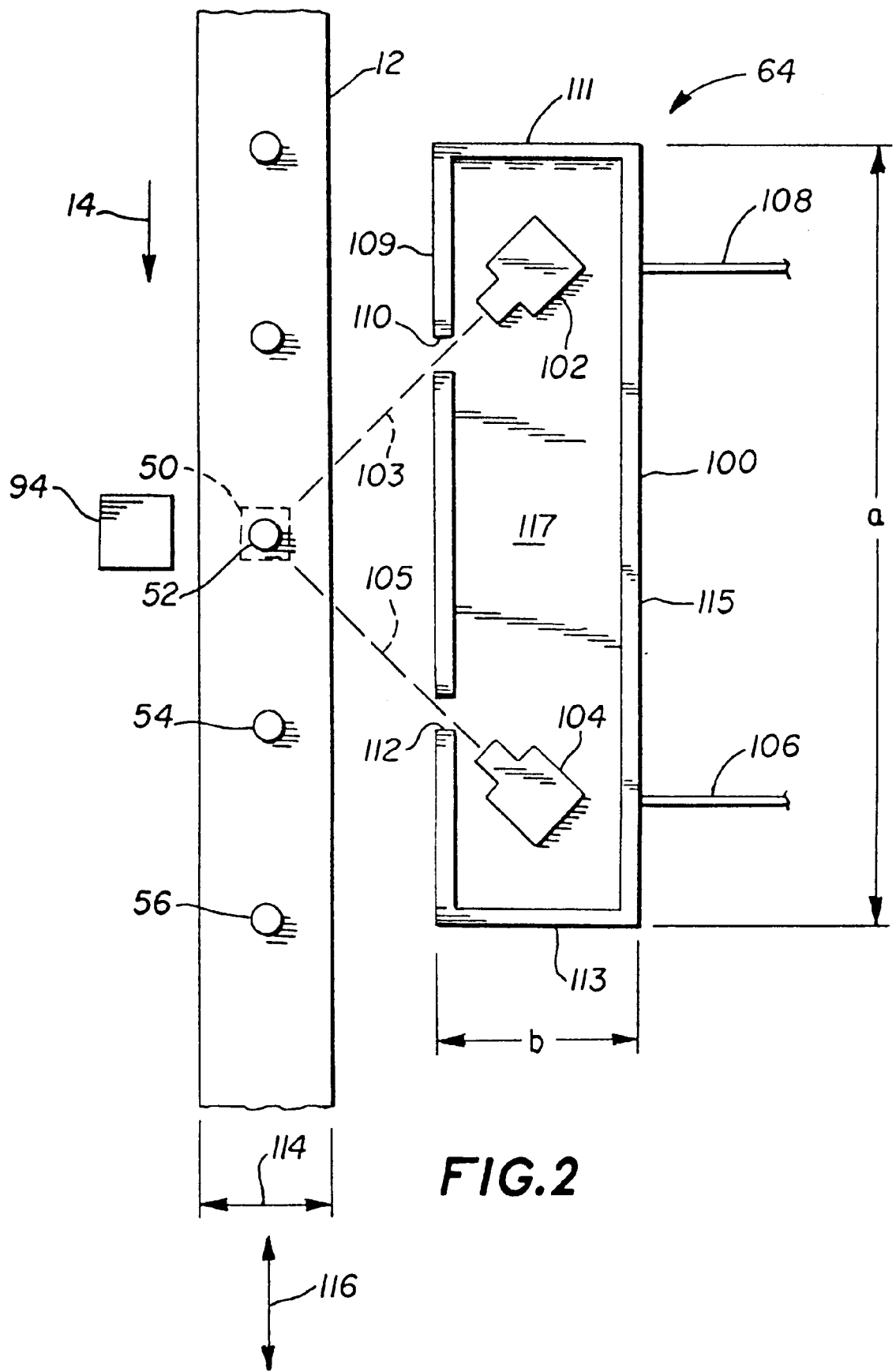
FIG. 2 is a schematic top plan view of a hot bottle inspection apparatus with its top member removed for clarity and a portion of an associated conveyor belt.

As best illustrated by FIG. 2, the hot bottle inspection apparatus 64 comprises a housing 100. This housing contains a first imaging device 102 and a second imaging device 104.

Housing 100 may comprise front wall 109, first side wall 111, second side wall 113 and rear wall 115. The housing 100 may also include a top wall member, not shown. Housing 100 may have a length "a" of about 4', a width "b" of about 2' and a height of about 4'.

A data connection 106 is provided for transmitting the images acquired by first imaging device 102 and second imaging device 104 to remote computer 66. Housing 100 may be insulated in order to withstand the intense heat of the hot end area 80. Pressurized cooling fluid is supplied to the housing 100 via fluid line 108. Fluid line 108 may supply a flow of pressurized filtered air to the housing for cooling purposes in a manner as described in the previously referenced U.S. Pat. No. 5,437,702.

Opening 110 is provided in the front wall 109 of housing 100 to allow a line of sight 103 between the bottle 52 and first imaging device 102. Opening 112 is provided in the front wall 109 of housing 120 to allow a line of sight 105 between bottle 52 and second imaging device 104. Leaving these areas open, rather than covering them with clear panels, obviates the problem previously described regarding the panels becoming dirty. Openings 110 and 112 may each measure about 1 inch by 1 inch.

FIG. 2 shows a series of bottles such as bottles 52, 54 and 56 moving along conveyor 12 past housing 100 in the direction indicated by the arrow 14. As a bottle, such as bottle 52 in FIG. 2, moves into the target site 50, strobe light 94 is energized thus causing the imaging devices 102 and 104 to produce images of the bottle 52. The computer 66 then combines the images to arrive at a composite image as is well-known.

As previously described, the bottle forming "I.S. machine" generates signals in a well-known manner. Since the number of bottle molds within the I.S. machine is known, computer 66 can use these pulses to determine when each bottle is formed and thus when to energize the strobe light 94. Since the order of bottles on the conveyor 12 corresponds to the mold order in the I.S. machine, the computer 66 is also able to correlate acquired image data to the I.S. machine mold which formed the bottle being imaged. In this manner, bottle conditions detected by the hot bottle inspection apparatus can be correlated to a specific mold.

In one example, the I.S. machine may generate one pulse per revolution and may produce 10 bottles per revolution. In this case, computer 66 would know that 10 bottles are produced per I.S. machine pulse. The use of this type of bottle tracking system obviates the need for photosensors or other physical detectors which would be adversely affected by exposure to the harsh environment of the hot end.

In operation, cooling fluid is introduced through fluid line 108 at a rate great enough to prevent dirt and outside air from the bottle hot end 80 from entering the housing 64. The fluid entering the housing 100 maintains the interior of the housing at a pressure higher than that of the outside atmosphere. Although fluid will escape through the openings 110 and 112, new cooling fluid is introduced through fluid line 108 at a rate great enough to compensate for this escaping fluid. This arrangement eliminates the need for a discharge orifice in the housing as disclosed in the previously referenced U.S. Pat. No. 5,437,702. This arrangement also eliminates the need for the maintenance previously required for cleaning the clear panels. The cooling fluid may be in the form of compressed air.

Figure 3:
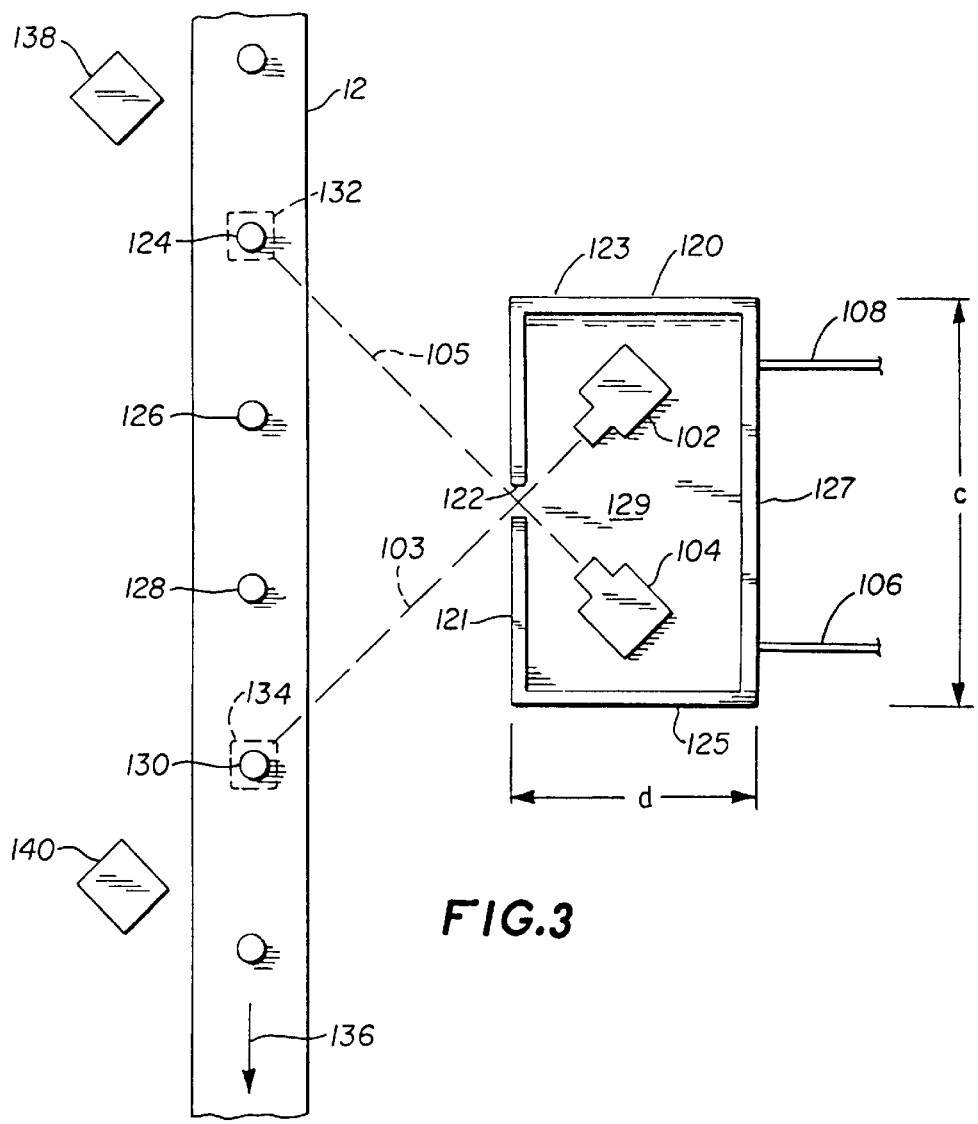
FIG. 3 is a schematic top plan view of another embodiment of the hot bottle inspection apparatus shown in FIG. 2.

FIG. 3 illustrates an alternative embodiment of the invention in which a single opening 122 is provided in a housing 120 to accommodate both lines of sight 103 and 105. Providing only one opening is advantageous since less cooling air escapes from one opening than escapes from two openings. Since less cooling air escapes, less cooling air needs to be supplied to the housing 120.

Housing 120 contains a first imaging device 102 and a second imaging device 104. Housing 120 may comprise front wall 121, first side wall 123, second side wall 125 and rear wall 127. The housing 120 may also include a top wall member, not shown. Housing 120 may have a length "c" of about 2', a width I"d" of about 2' and a height of about 4'. A data connection 106 is provided for transmitting the images acquired by first imaging device 102 and second imaging device 104 to remote computer 66. Housing 120 may be insulated in order to withstand the intense heat of the hot end area 80. Pressurized cooling fluid is supplied to the housing 120 via fluid line 108. Fluid line 108 may supply a flow of pressurized filtered air to the housing for cooling purposes as described in the previously referenced U.S. Pat. No. 5,437,702.

An opening 122 is provided in the front wall 121 of housing 120 to allow a line of sight 103 between the first imaging device 102 and target site 134 located on conveyor 12. Opening 122 also allows a line of sight 105 between second imaging device 104 and target site 132 located on the conveyor 12. The imaging devices 102 and 104 are configured within housing 120 so that their lines of sight 103 and 105 cross in the vicinity of the opening 122 as shown in FIG. 3. Configuring the imaging devices in this manner allows the use of one relatively small opening 122 in housing 120, thus reducing the loss of cooling air from housing 120.

Because of the configuration of imaging devices 102 and 104 described above, each imaging device will image a different bottle at any given time. In order to combine the proper images from imaging devices 102 and 104, the remote computer 66 stores image data for a particular bottle from imaging device 104 until the same bottle moves into a position where it is imaged by imaging device 102. The computer then assembles the image data from the two imaging devices 102 and 104 to obtain complete data for each bottle.

FIG. 3 shows a series of bottles such as bottles 124, 126, 128, and 130 moving along conveyor 12 past housing 120 in the direction indicated by the arrow 136. As a bottle, such as bottle 124 in FIG. 3, moves into the target site 132, strobe light 138 is energized thus causing imaging device 104 to produce an image of the bottle 124. This image is stored by the computer 66 until the bottle 124 moves into the target site 134 and strobe light 140 is energized, thus causing imaging device 102 to produce an image of the bottle 124. The computer then combines the stored image from imaging device 104 with the newly acquired image from imaging device 102 to arrive at a complete image of bottle 124. This process is repeated for each bottle conveyed by the conveyor 12. Bottles are tracked by the computer 66 using I.S. machine pulses in a manner as previously described.

Opening 122 may measure about 1" inch by 1 inch. In operation, cooling fluid is introduced through fluid line 108 at a rate great enough to prevent dirt and outside air from the bottle hot end 80 from entering the housing 120. The fluid entering the housing 120 maintains the interior of the housing at a pressure higher than that of the outside atmosphere. Although fluid will escape through the opening 122, new cooling fluid is introduced through fluid line 108 at a rate great enough to compensate for this escaping fluid. It has been found that supplying cooling fluid in the form of compressed air at a rate of about 2 standard cubic feet per minute is sufficient given the size of the housing 120 and the opening 122 as described above. The compressed air may be supplied to housing 120 at a temperature of about 30 degrees Celsius.

With respect to either housing 100 or housing 120, the imaging devices 102 and 104 may be located so that the center of their lenses are vertically aligned with the plane of the top of the conveyor 12. This results in the imaging devices being located substantially below the plane of the conveyor. Since heat rises, this location is cooler and thus less damaging to the imaging devices. This location also allows the plane of the conveyor to be conveniently used as a reference plane when analyzing bottle image data.

Figure 12:
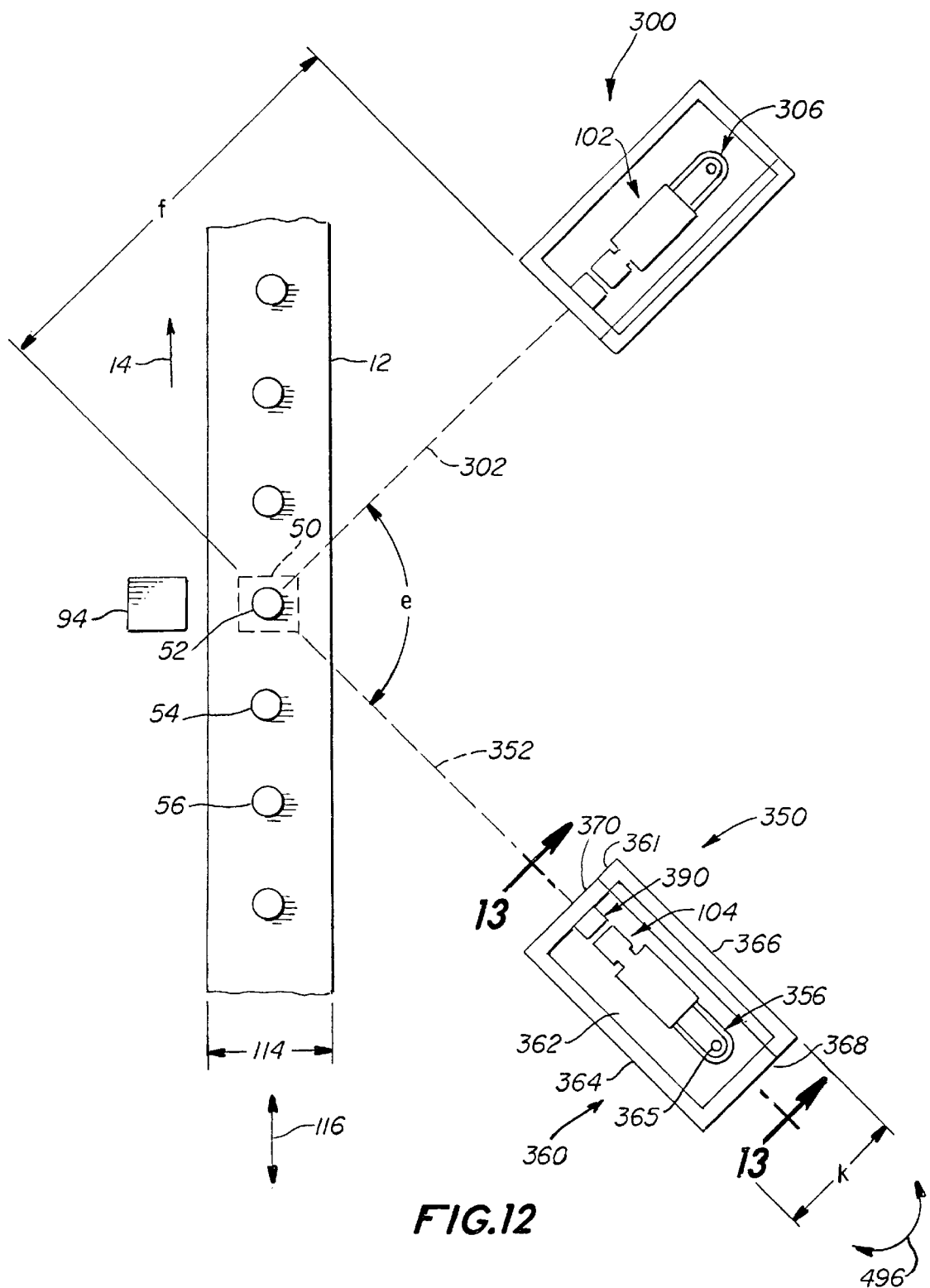
FIG. 12 is a schematic top plan view of another embodiment of a hot bottle inspection apparatus with its top member removed for clarity and a portion of an associated conveyor belt.

In another embodiment, the hot bottle inspection system housing may actually comprise two separate housing units, one for each imaging device 102, 104, as generally shown, for example, in FIG. 12. The use of two separate housings may make personnel access to the bottle line easier in some situations.

Air Loss Reduction

As previously described with reference to FIGS. 2 and 3, the housings 100 and 120 are pressurized via cooling air supplied through the fluid line 108. Pressurized air within the housings is then allowed to escape through the unobstructed housing openings (110 and 112 in the housing 100, FIG. 2, and 122 in the housing 120, FIG. 3). This escaping air prevents dirt and other contaminants from entering the housings 100, 120 through the openings 110, 112 and 122.

Although the pressurized housings described above generally function well, it has been found that, due to the size of the openings 110, 112 and 122, a relatively large amount of compressed cooling air must be supplied to the housings via the line 108 in order to maintain an adequate pressure differential and air flow through the openings. It has also been found that eddy currents sometimes form near the edges of the openings 110, 112 and 122, causing a small amount of outside air, dirt and other contaminants to be drawn into the housings 100, 120.

Another embodiment of the hot bottle inspection system which addresses the problems described above is illustrated in FIGS. 12–14. Referring now to FIG. 12, it can be seen that two separate housings 300, 350 may be provided to house the image generating devices 102, 104, respectively. The housings 300, 352 may be arranged near the hot bottle conveyor 12 as shown. A line of sight 302 may extend between the imaging device 102, housed withing the housing 300, and a target sight 50 located on the conveyor 12 in a manner similar to that previously described. A line of sight 352 may extend between the imaging device 104, housed within the housing 350, and the target sight 50. The lines of sight 302, 352 may form an angle "e" of about 90 degrees with respect to each other. Each housing 300, 352 may be located at a distance "f" from the target area 50 of about twelve inches, measured along the respective line of sight 302, 352, as shown in FIG. 12.

Each of the image generating devices 102, 104 may be connected to a data connection line 306, 356, respectively, in order to connect the image generating devices to a remote computer, in a similar manner to that previously described with respect to the data connection line 106.

The housings 300, 350 may be substantially identical to one another. Accordingly, only the housing 350 will be described in further detail herein, it being understood that the housing 300 may be constructed in a substantially identical manner.

Referring to FIG. 12, it can be seen that the housing 350 may comprise a two-piece assembly comprising a unitarily formed box portion 360 and a cover member 366 which, when assembled, together form a generally parallelepiped shaped structure. The box portion 360 may include a bottom wall 362; a front wall 370 extending upwardly from the bottom wall 362 at a substantially right angle thereto; a rear wall 368 extending upwardly from the bottom wall 362 and being substantially parallel to the front wall 370; a side wall 364 connecting the bottom wall 362, the front wall 370 and the rear wall 368 and being substantially perpendicular to the bottom wall 362, the front wall 370 and the rear wall 368; and a top wall 380, FIG. 13, substantially parallel to the bottom wall 362 and connecting the front wall 370, the side wall 364 and the rear wall 368.

The cover member 366 may attach to the box portion 360 via screws (not shown) or via any conventional attachment method. An O-ring gasket (not shown) may be provided between the box portion 360 and the cover member 336 in order to provide an airtight seal between the box portion 360 and the cover member 366 in a conventional manner. In this manner, the cover member 366 may be removed to provide access to the imaging device 104 and to the other contents of the housing 350 and replaced in order to provide an airtight housing. When the cover member 336 is attached to the box portion 360, a seam 361 is formed between the cover member 336 and the box 360 as shown in FIGS. 12 and 13.

Figure 13:
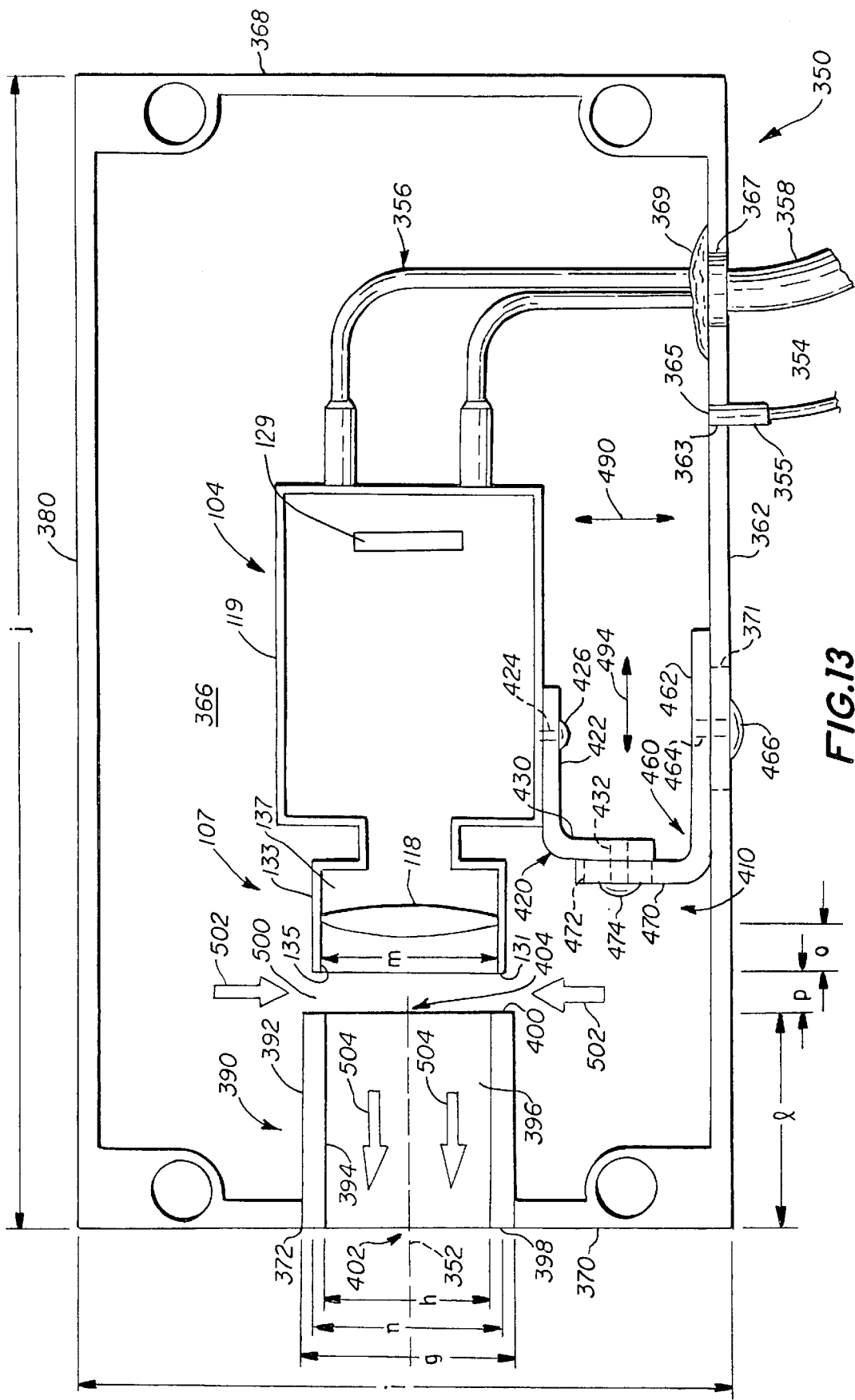
FIG. 13 is a cross-sectional elevation view of a hot bottle inspection apparatus housing taken along the line 13—13 in FIG. 12.
Figure 14:
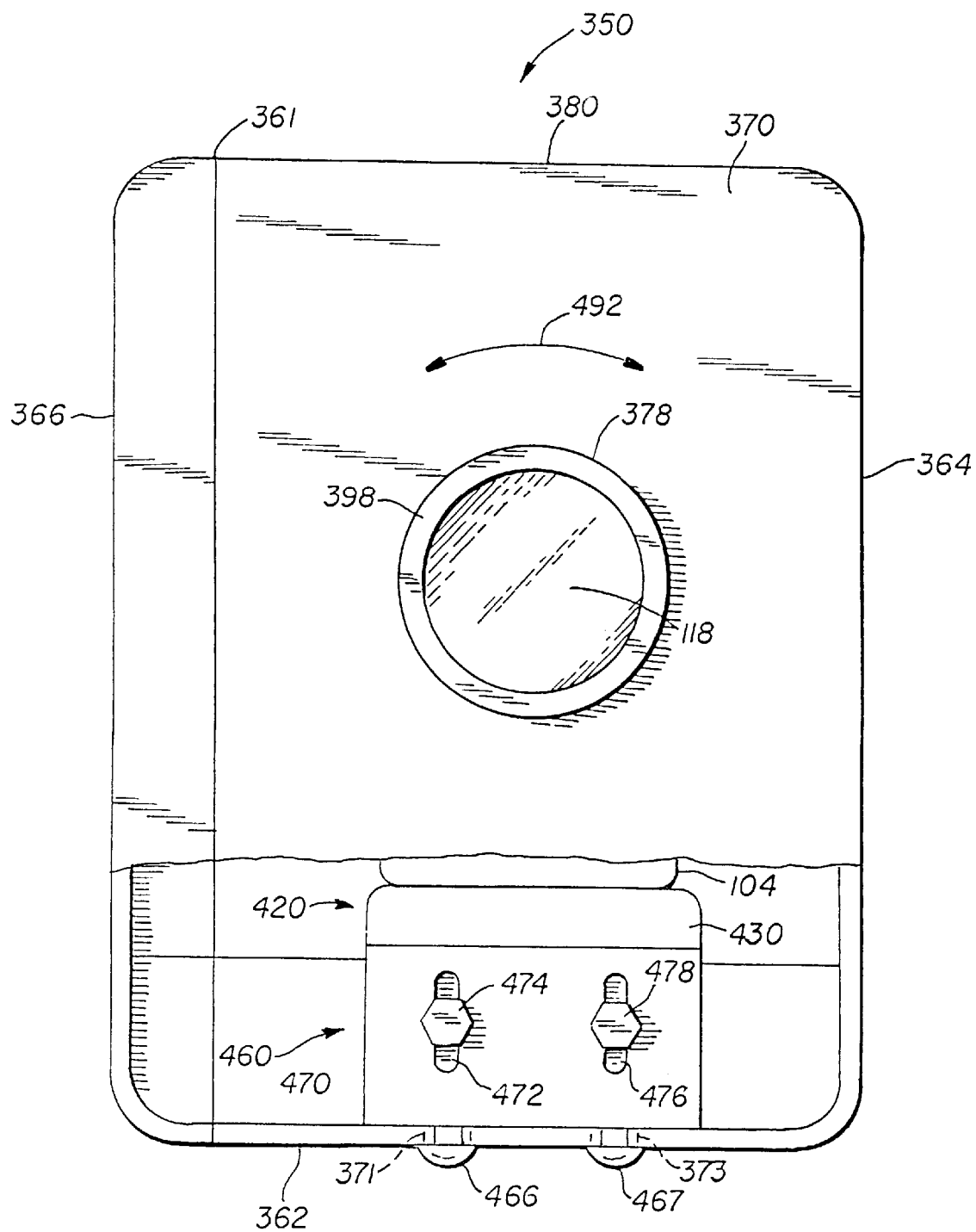
FIG. 14 is front elevation partial cutaway view of the hot bottle inspection apparatus housing of FIG. 13.

As best shown in FIGS. 13 and 14, a hole 372 may be formed through the housing front wall 370. The hole 372 may be generally circular and have a diameter "g" of about 1.0 inch, FIG. 13.

Referring again to FIG. 13, the housing 350 may be provided with a cooling fluid supply line 354 in order to supply pressurized cooling air in a manner as previously described with respect to the cooling fluid supply line 108. The fluid supply line 354 may terminate in a fitting 355 which may be threadingly engaged within a threaded hole 363 formed in the housing bottom wall 362. The hole 363 terminates at the inner surface of the housing bottom wall 362 to form an orifice 365 through which compressed cooling air enters the interior of the housing 350.

The data connection lines 356 may pass through a hole 367 formed in the housing bottom wall 362. Exteriorly of the housing 350, the data connection lines 356 may be carried within a protective conduit 358 as shown in a conventional manner. The hole 367 may be sealed at the inner surface of the housing bottom wall 362 by applying a quantity of sealant material 369 as shown in order to prevent pressurized cooling air within the interior of the housing 350 from escaping through the hole 367 around the data connection lines 356. The sealant material 369 may be a sealant material such as a high temperature rubber or may be any other conventional type of sealant material The housing 350 may be constructed of cast aluminum, with the walls 362, 364, 368, 370, 380 and the lid member 366 each having a wall thickness of about 3/16 inch. With the exception of the opening 372 formed in the front wall 370 and the openings 363 and 367 in the bottom wall 362 to accommodate the various connections, as previously described, the housing 350 may be of the type known generally in the industry as a "NEMA 12 rated enclosure" and generally available from The Hoffman Engineering Company of Anoka, Minn. and sold as Model No. PX12. The housing 350 may have an overall height "i" of about 6.0 inches, an overall length "j" of about 12.0 inches, FIG. 13, and an overall width "k" of about 3.0 inches, FIG. 12.

Referring again to FIG. 13, an annular sleeve member 390 may be attached to the housing front wall 370 in the vicinity of the opening 372 as shown. The sleeve member 390 may be formed as an annular cylinder having an outer surface 392 and an inner surface 394 forming a cylindrical passageway 396 therewithin. A front annular surface 398 extends between the sleeve member outer and inner surfaces 392, 394 at a forward end of the sleeve member 390. In a similar manner, a rear annular surface 400 extends between the sleeve member outer and inner surfaces 392, 394 at a rearward end of the sleeve member 390. The cylindrical passageway 396 terminates at a forward open end 402 which is surrounded by the sleeve member front annular surface 398 and at a rear open end 404 which is surrounded by the sleeve member rear annular surface 400. The sleeve member outer surface 392 may have a diameter which is substantially equal to the housing front wall opening 372 diameter "g" as previously described. The sleeve member inner surface 394 may have a diameter "h" of about 7/8 inch. Accordingly, with the example dimensions set forth above, the annular sleeve member 390 may have a wall thickness of about 0.0625 inches. The sleeve member 390 may have a length "l" of about 1.0 inch, extending between the front surface 398 and the rear surface 400. The sleeve member 390 may be constructed of a phenolic material and may be formed in any conventional manner such as by machining.

The sleeve member 390 may be attached to the housing front wall 372 in any suitable manner which provides an air-tight seal between the sleeve member and the front wall. In a preferred method, however, as shown in FIGS. 12 and 13, attachment may be accomplished by press-fitting the sleeve member 390 into the housing front wall opening 372.

Turning again to FIG. 13, the imaging device 104 may be mounted within the housing 350 via an adjustable mounting assembly 410. Adjustable mounting assembly 410 generally includes an upper L-shaped bracket 420 and a lower L-shaped bracket 460. Upper bracket 420 is formed from a first, generally horizontally disposed leg portion 422 and an integrally formed generally vertically disposed leg portion 430. A pair of through holes 424 (only one is shown) are formed in the upper bracket horizontal leg 422 as shown. A pair of bolts 426 (only one is shown) may be passed through the holes 424 and threadingly engaged with a lower portion of the imaging device body portion 119, as shown, in order to securely attach the imaging device 104 to the upper bracket 420. The upper bracket vertical leg 430 may include a pair of threaded holes 432 (only one is shown) for a purpose as will be described hereafter.

Lower bracket 460 is formed from a first, generally horizontally disposed leg portion 462 and an integrally formed generally vertically disposed leg portion 470. A pair of slotted holes 472 and 476, FIGS. 13 and 14, may be provided in the lower bracket vertical leg 470 as shown. A pair of bolts 474 and 478 may be passed through the lower bracket slotted holes 472, 476, respectively, and threadingly engaged within the upper bracket threaded holes 432 in order to securely attach the upper bracket vertical leg 430 to the lower bracket vertical leg 470.

Lower bracket horizontal leg 462 may include a pair of threaded holes 464 (only one is shown). A pair of bolts 466, 467, FIGS. 13, 14, are passed through a pair of slots 371, 373 formed in the housing lower wall 362 as shown in FIGS. 13 and 14. The bolts 466, 467 threadingly engage within the lower bracket horizontal leg threaded holes 464 in order to securely attach the lower bracket 460 to the housing lower wall 362.

In the manner described above, the image generating device 104 is securely attached to the housing 350 via the adjustable mounting assembly 410. The adjustable mounting assembly 410 allows the position of the image generating device 104 to be adjusted relative to the housing 350 in several degrees of movement as will now be described in detail.

As can be appreciated, when the bolts 474, 478 are sufficiently loosened, the slotted holes 472, 476 allow the upper bracket 420, along with the attached imaging device 104, to be vertically adjusted with respect to the housing 350 and attached lower bracket 460, i.e., adjusted in the directions indicated by the arrow 490 in FIG. 13. Due to the clearance between the slotted holes 472, 476 and the bolts 474, 478, respectively, loosening the bolts 474, 478 also allows limited rotational adjustment of the image generating device 104 in the directions indicated by the arrow 492 in FIG. 14.

As can further be appreciated, when the bolts 466, 467 are sufficiently loosened, the slotted holes 371, 373, respectively, allow the entire adjustable mounting assembly 410, along with the attached imaging device 104, to be horizontally adjusted with respect to the housing 350, i.e., adjusted in the directions indicated by the arrow 494 in FIG. 13. Due to the clearance between the slotted holes 371, 373 and the bolts 466, 467, respectively, loosening the bolts 466, 467 also allows limited rotational adjustment of the adjustable mounting assembly 410 and the attached image generating device 104 relative to the housing 350 in the directions indicated by the arrow 496 in FIG. 12.

The adjustable mounting assembly 410, thus, allows the imaging device 104 to easily be aligned with the sleeve member 390. It is noted that, although a preferred adjustable mounting assembly has been described in detail above, the imaging device 104 may, alternatively, be mounted to the housing 350 via any type of adjustable mounting assembly which allows for adjustable movement of the imaging device 104 relative to the housing 350.

In a similar manner to the housings 100, FIG. 2, and 120, FIG. 3, previously described, the housing 350 may be supplied with pressurized cooling air in order to maintain the interior of the housing at relatively low temperature and, thus, protect the image generating device 104 from the heat of the hot end of the bottle manufacturing production line. Air entering the housing 350 through the cooling fluid supply line orifice 365 maintains the interior of the housing 350 at a higher pressure than the exterior of the housing. In a similar manner to the housings 100 and 120, air escapes from the interior of the housing 350 through the opening 372 formed in the front wall 370 of the housing. Unlike the housings 100 and 120, however, the housing 350 includes a mechanism for controlling the amount of air which escapes and for preventing the formation of eddy currents which sometimes occur in the vicinity of air flow openings.

Referring again to FIG. 13, it can be seen that the image generating device 104 may include a body portion 119 and a lens assembly 107 located at the forward end of the housing portion 119, in a conventional manner. The lens assembly 107 may be formed as an annular cylinder having an outer surface 133 and an inner surface 135 forming a cylindrical passageway 137 therewithin. A front annular surface 131 extends between the lens assembly outer and inner surfaces 133, 135 at a forward end of the lens assembly 107. The lens assembly outer surface 133 may have a diameter "n" of about 1.0 inch. The lens assembly inner surface 135 may have a diameter "m" of about 15/16 inches. Accordingly, with the example dimensions set forth above, the lens assembly cylinder may have a wall thickness of about 1/32 inch. The lens assembly 107 may also include a lens 118. The lens 118 may be located within the lens assembly cylindrical passageway 137 in a conventional manner, and may be spaced a distance "o" of about 1/4 inch from the lens assembly front annular surface 131 as shown. A photoelectric device 129 may also be located within the housing portion 119. Photoelectric device 129 may be operatively associated with the lens 118 in a conventional manner and may, for example, be a charge couple device as described herein.

As can be appreciated with reference to FIG. 13, a restricted airflow opening 500 is formed between the sleeve member rear annular face 400 and the imaging device lens assembly forward annular surface 131. In operation, pressurized air within the housing 350 passes through the restricted opening 500 and enters the sleeve member cylindrical passageway 396 through the sleeve member rear open end 404 as indicated by the airflow arrows 502. Once within the cylindrical passageway 396, the air then moves in a direction as indicated by the airflow arrows 504 and subsequently exits the housing 350 through the sleeve member forward open end 402.

The amount of restriction imposed upon the exiting air may be controlled by adjusting the distance "p" between the lens assembly forward annular surface 131 and the sleeve member rear annular surface 400. As can be appreciated, the distance "p" may be easily varied by loosening the bolts 466, 467 and sliding the adjustable mounting assembly 410 and attached image generating device 104 in the directions 494 in a manner as previously described.

Preferably, the sleeve member 390 is sized such that the sleeve member rear annular surface 400 fully encompasses the lens assembly forward annular surface 131. In other words, the sleeve member 390 is preferably sized such that the sleeve member inside diameter "h" is less than the lens assembly inside diameter "m" and the sleeve member outside diameter "g" is greater than the lens assembly outside diameter "n". When so configured, the effective area of the restricted opening 500 will be equal to the circumference of the lens assembly inner surface 135 (i.e., the circumference dictated by the diameter "m") multiplied by the distance "p". Accordingly, the effective area of the restricted opening 500 may be calculated according to the following equation:

$$m \times \Pi \times p$$

In one example, the distance "p" may be set to about 0.02 inches. According to the above equation, with the exemplary dimension "m" of about 15/16 inches, as set forth previously, this distance "p" of about 0.02 inches yields an effective area of about 0.059 square inches. It has been found that this arrangement provides satisfactory air flow through the housing 350 when air is supplied at a pressure of about 25 psi. Of course, with the novel design set forth above, the distance "p", and thus the effective area of the restricted opening 500, may easily be varied in order to compensate for variables such as cooling fluid supply pressure and external heat.

Like the housings 100 and 120, previously described, the housing 350 provides an unobstructed line of sight 352 between the imaging device lens 118, FIG. 13, and the target site 50, FIG. 12, located along the conveyor 12. This arrangement eliminates window panels made of glass or other materials which are prone to dirtying from the contaminated hot-end environment of a bottle production line. The housing 350, however, differs from the housings previously described in that it provides a mechanism for controlling the amount of air which escapes from the housing.

The annular sleeve 390 not only provides air restriction to control the amount of air escaping from the housing 350, but also serves to space the imaging device lens 118 from the contaminated environment exterior to the housing 350. As can be appreciated from an examination of FIG. 13, increasing the length "l" of the sleeve member 390 will cause the imaging device lens 118 to be further spaced from the exterior environment. Increasing the distance "l" too much, however, may cause the sleeve member inner surface 394 to interfere with the imaging ability of the lens 118. It has been found that the exemplary distance "l" of about 1.0 inch, as set forth above, provides adequate spacing of the lens 118 from the exterior environment while causing little if any interference with the optical ability of the lens.

It has further been found that use of the sleeve member 390, as described above, also eliminates eddy currents which have sometimes been found to form around the openings of the housings 100, 120. These eddy currents cause a small amount of contaminated air from the exterior environment to be drawn into the housings 100, 120, thus exposing the imaging device or devices housed within to be exposed to the contaminated air. Thus, by eliminating such eddy currents, the sleeve member 390 serves to maintain the imaging device housed within the housing 350 in a cleaner fashion.

Correction for Orientation

The general technique of imaging of bottles onto photoelectric devices such as CCDs (charge couple devices) and the subsequent analysis of the data signal to measure various bottle parameters is well known in the art. It has been found, however, that measuring bottles at the hot end 80 of a bottle production line 10 presents problems which have not previously been solved.

As a result of the elevated temperature of the bottles at the hot end 80 of the production line 10, any engagement of the bottles by an inspection machine, as is conventional with cold end inspectors, would result in deformation of the bottle surface producing an ascetically unacceptable bottle. This, along with the relatively high speed of bottle production line conveyors means that the bottles are often bouncing when a hot end inspection process is being carried out. Due to this bouncing, the exact orientation of a bottle when it is being inspected cannot be accurately determined.

The present invention overcomes this difficulty by first analyzing the bottle image to find a known feature of the bottle. The orientation of this feature, and thus the entire bottle, is then determined. The desired bottle measurements are then made and adjusted relative to the orientation of the known feature. This allows true measurements to be achieved even on randomly oriented bottles, such as bouncing bottles.

One example of a particular physical parameter which may be determined by the imaging device of the present invention is the degree to which the sidewalls of a bottle are perpendicular to its base.

Figure 4:
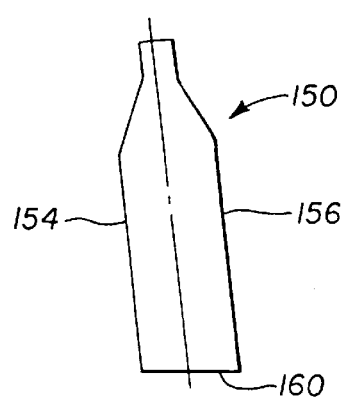
FIG. 4 is a schematic front elevation view of a defective bottle.
Figure 5:
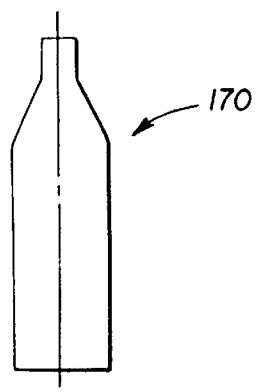
FIG. 5 is a schematic front elevation view of a non-defective bottle.

FIG. 4 schematically illustrates a bottle 150, the sidewalls 154, 156 of which are not perpendicular to its base 160. This defective condition is commonly referred to as "lean" and bottles exhibiting this condition are commonly referred to as "leaners". It should be noted that the lean depicted in FIG. 4 has been greatly exaggerated for purposes of illustration. FIG. 5 shows a non-defective bottle 170 exhibiting no perceptible lean.

The lean measured by the hot bottle inspection apparatus 64 may be compared with pre-determined values and any bottle having parameters exceeding a fixed tolerance from this value is determined by the system to be defective. It is noted, however, that, in the case of leaners, detecting even a slight lean that is within tolerance can be useful to bottle line process control. Leaners generally occur when the bottle formation temperature becomes too high. This high temperature causes the glass to be too soft and, thus, leaners occur. Accordingly, early detection of in-tolerance leaners can provide the bottle line operators with information indicating that the bottle formation process is becoming too hot. Adequate corrective action can then be taken to prevent further overheating and the occurrence of reject-level leaners.

Referring again to FIG. 2, it can be seen that first imaging device 102 and second imaging device 104 image the bottle 52 from different directions. This ensures that a leaner will be detected even if it is leaning directly toward or away from one of the imaging devices. In such a case, the other imaging device would still detect the lean.

Figure 6:
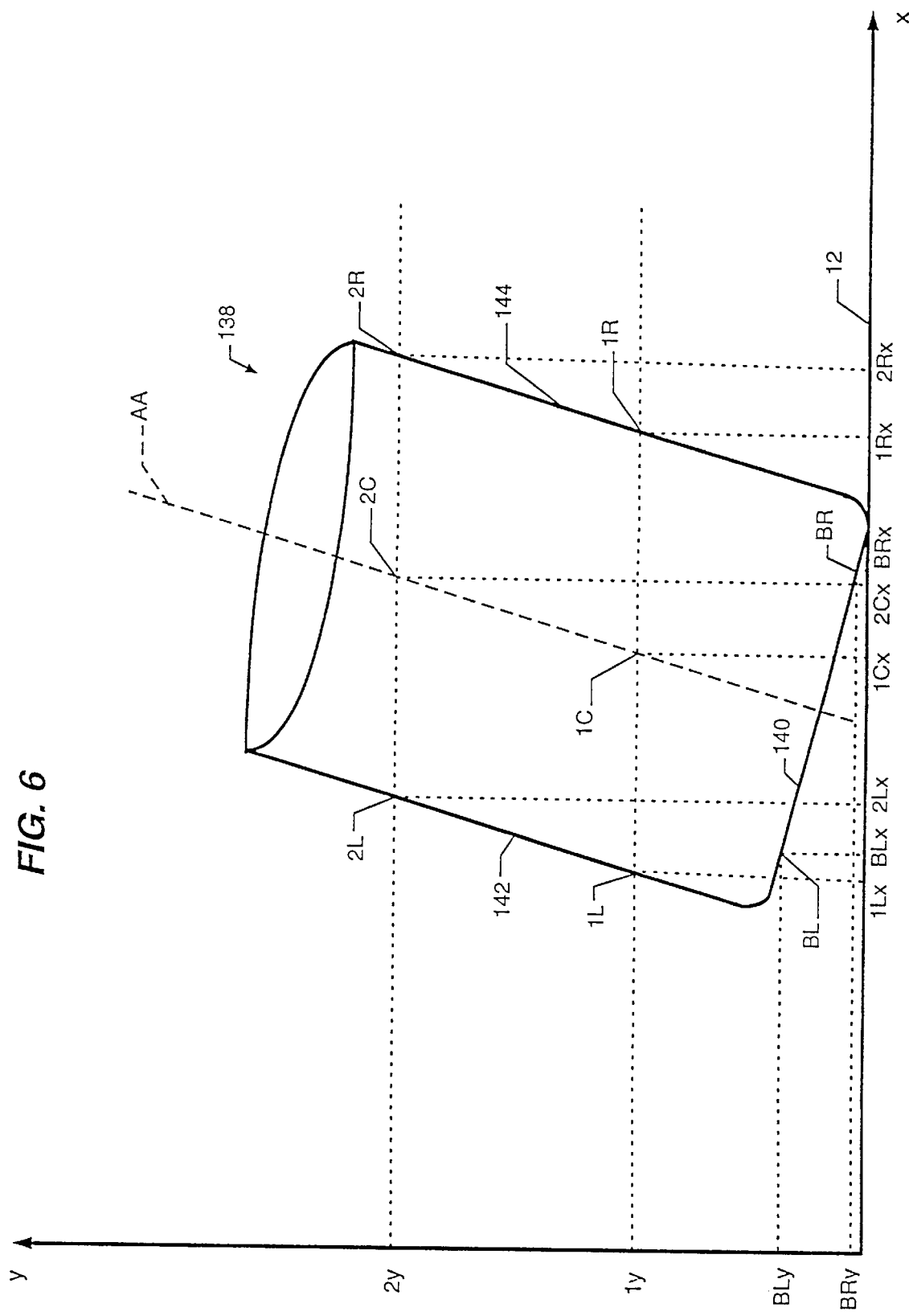
FIG. 6 is a schematic front elevation view illustrating the process used to analyze a bottle that is randomly oriented.

The method employed to compensate for bottle orientation will now be described in detail. FIG. 6 illustrates an image of a bottle 138 generated, for example, by first imaging device 102. The bottle 138 was imaged while it was bouncing and thus is shown in a random orientation in FIG. 6.

Bottle lean may be characterized by the deviation of the center line AA of a bottle from vertical. In other words, deviation may be described as the difference between the horizontal location of the bottle centerline AA near the base 140 of the bottle and the horizontal location of the bottle centerline AA near the top of the bottle. If these horizontal locations are identical, then the bottle exhibits no lean. If they are different, however, then the bottle is a leaner and the magnitude of this horizontal difference characterizes the amount of lean.

Figure 7:
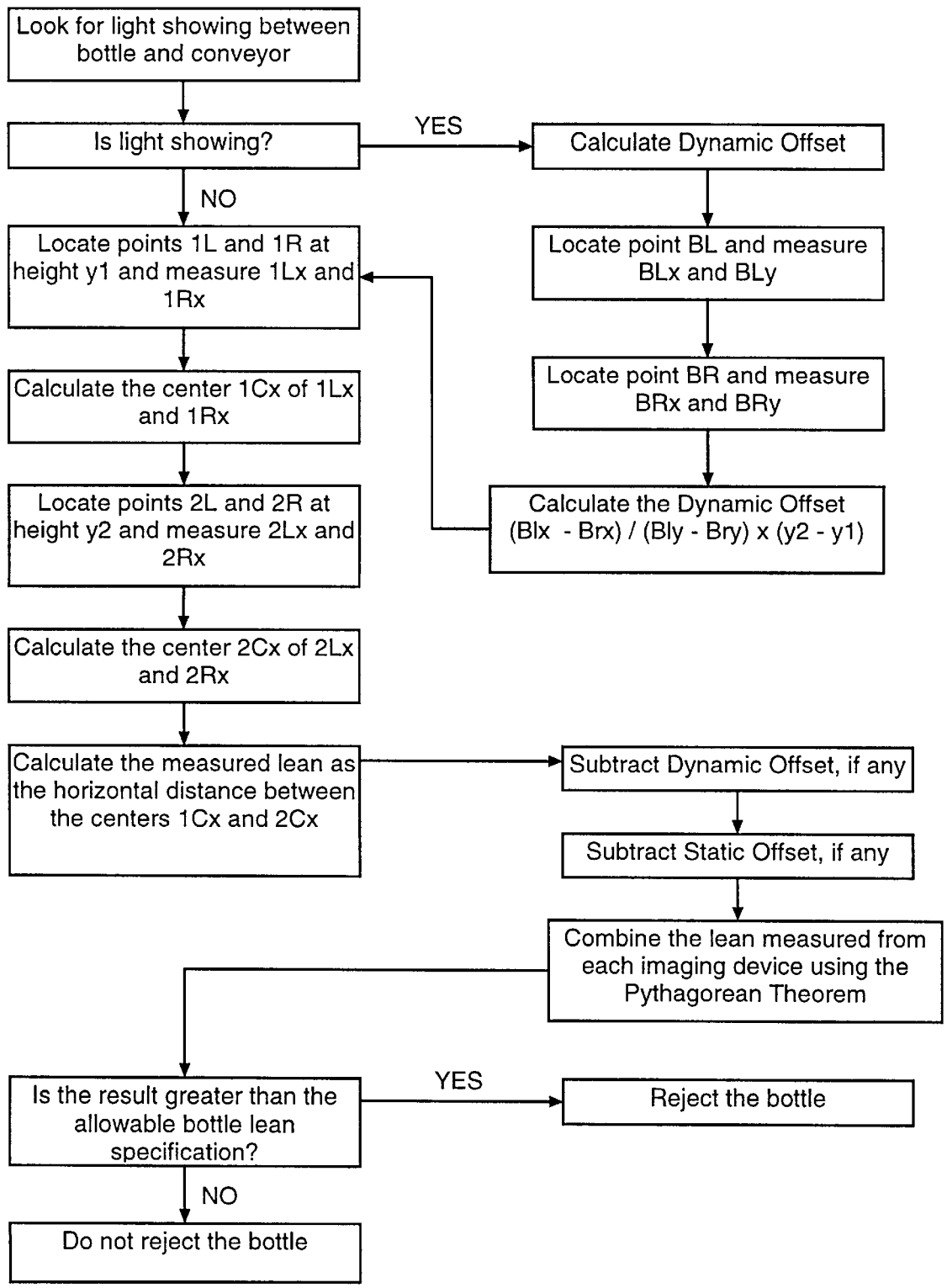
FIG. 7 is a flow chart illustrating the steps taken to compensate for randomly oriented bottles.

A specific method for measuring lean will now be described in detail with reference to FIG. 6. FIG. 7 is a block diagram illustrating this method.

First, the image is analyzed to determine if there is any light showing beneath the base 140 of the bottle image 138. If no light is showing, this means that the bottle is setting flat on the conveyor 12 and is not bouncing. If light is showing, as in the case of FIG. 6, this means that the bottle is not setting flat on the conveyor and compensation must be made for the orientation of the bottle due to bouncing.

If the bottle is bouncing, then the "dynamic offset" is calculated. The dynamic offset is the amount of measured lean caused by the orientation of the bottle. To calculate the dynamic offset, the base 140, left edge 142 and right edge 144 of the bottle are first located. Next a point "BL" is located on the base 140 of the bottle. The point BL is defined as a point located along the base 140 of the bottle at a predetermined distance in from the left edge 142 of the bottle. It is not desirable to use the actual corner of the bottle for the point BL since bottle corners are often rounded, making a precise location in this area difficult.

A point "BR" is then located on the base 140 of the bottle. The point BR is defined as a point located along the base 140 of the bottle at a predetermined distance in from the right edge 144 of the bottle. Both of the points BL and BR may be located the same distance in from their respective edges. This distance may, for example, be about 0.5 inches.

The dynamic offset is then calculated as:

$$(BLx-BRx)/(BLy-BRy) \times (2y-1y)$$

where BLx is the location along the x-axis of point BL, BRx is the location along the x-axis of point BR, BLy is the location along the y-axis of point BL, BRy is the point along the y-axis of point BR and 2y and 1y are predetermined heights above the plane of the conveyor 12 used to measure bottle lean as further described below.

After the dynamic offset is calculated (or if no dynamic offset is calculated because the bottle was not bouncing when imaged), points 1L and 1R are located. Point 1L is the point where the left edge 142 of the bottle image is found at a predetermined height 1y above the plane of the conveyor 12. Point 1R is the point where the right edge 144 of the bottle image is found at the same height 1y above the plane of the conveyor 12. For purposes of example, the height 1y may be about 1.25 inches.

The location of the horizontal center 1C of points 1L and 1R is then calculated as the point having a y location equal to 1y and an x location equal to:

$$(1Lx+1Rx)/2$$

where 1Lx is the location along the x-axis of point 1L and 1Rx is the location along the x-axis of point 1R.

Next, points 2L and 2R are located. Point 2L is the point where the left edge 142 of the bottle image is found at a predetermined height 2y above the plane of the conveyor 12. Point 2R is the point where the right edge 144 of the bottle image is found at the same height 2y above the plane of the conveyor 12. For purposes of example, the height 2y may be about 6 inches.

The location of the horizontal center 2C of points 2L and 2R is then calculated as the point having a y location equal to 2y and an x location equal to:

$$(2Lx+2Rx)/2$$

where 2Lx is the location along the x-axis of point 2L and 2Rx is the location along the x-axis of point 2R.

The points 1Cx and 2Cx lie along the centerline AA of the bottle and, thus, together define the centerline AA. The measured lean is then calculated as the difference in horizontal location of the center points 1Cx and 2Cx:

$$2Cx-1Cx$$

Next, the dynamic offset, if any, is subtracted from the measured lean to arrive at the true bottle lean. Since the dynamic offset represents the lean attributable to the bottle's orientation on the conveyor, subtracting out this lean will result in the lean that is inherent in the bottle itself.

The above method is carried out for each of the imaging devices 102 and 104. The bottle lean calculated for each imaging device is then combined to arrive at a combined true bottle lean as will now be described.

Imaging devices 102 and 104 are arranged such that their lines of sight 103 and 105, respectively cross at right angles to one another, FIGS. 2 and 3. Since each imaging device can only measure lean perpendicular to its line of sight, this means that the lean measured by imaging device 102 will always be at a right angle to the lean measured by imaging device 104. Since two right angle component of the true lean are known, the Pythagorean theorem can be used to calculate the combined true lean as:

$$(L1^2+L2^2)^{1/2}$$

where L1 is the true lean calculated based on the image from first imaging device 102 and L2 is the true lean calculated based on the image from second imaging device 104.

The combined true bottle lean is then compared to the allowable specification. If the combined true lean exceeds the allowable lean, then the bottle is rejected by rejection device 68. If, however, the combined true lean is within acceptable limits, the bottle is allowed to continue on the conveyor 12 toward the cold end 82 of the bottle production line.

The combined true lean information may be made available to the bottle production line operators even in cases where the lean is found to be within allowable limits. This allows the operators to observe and to react to any trend in the combined true lean measurements. Increasing lean, for example, may indicate that the bottle forming process is becoming too hot. An operator, observing such an increase, can take appropriate steps to lower the temperature of the bottle forming process before bottles having rejection level defects are formed. Such feedback of bottle lean information, thus, allows avoidance of potential rejects. Alternatively, a computer may be used to observe and automatically react to such trend information.

In addition to the dynamic offset described above, a static offset may also be subtracted from the measured lean to arrive at the true bottle lean. Static offset is the offset measured when an in-specification bottle is placed flat on the conveyor 12, while the conveyor is not moving. Static offset accounts for errors in the hot bottle inspection system itself that do not change from bottle to bottle. For example, static offset may account for any misalignment between the imaging devices 102, 104 and the bottle conveyor 12.

Static offset may also account for lens aberration. Each imaging device 102, 104 contains a lens as is well-known. All lenses display some degree of aberration, or distortion in some areas of the lens. Static offset accounts for such aberration. Subtracting the static offset in this manner also allows less expensive lenses to be employed. Less expensive lenses tend to exhibit more aberration than do more costly lenses. Since this aberration is static and predictable, however, using a static offset, as described above, allows less expensive lenses to be used while still ensuring that accurate bottle lean information can be obtained.

Although the bottle inspection method has been described with respect to obtaining two center points 1C and 2C, it is noted that a greater number of points can be evaluated if desired. If a greater number of points are used, the lean can be calculated by taking the average of the individual leans calculated between each of the points. Using a greater number of points also facilitates the detection of other bottle abnormalities such as bulges. If a bulge exists in the sidewall of a bottle, this will cause the center point at this location to be offset from the other center points thus indicating that a problem exists in this area.

In addition to bottle lean information, the procedure described above may also be used to measure actual bottle dimensions at various locations. Once the bottle lean is known, the true bottle width, e.g., may be calculated using trigonometry. An example of such a calculation is described below with respect to FIG. 6.

For purposes of this example, the "lean angle" is the angle formed between the base 140 of the bottle and the conveyor 12. The lean angle may be calculated using any number of trigonometric functions and the bottle measurement data which has been collected as previously described. The lean angle may, for example, be calculated as follows:

$$\text{lean angle}=\tan^{-1}((BLy-BRy)/(BLx-BRx))$$

Once calculated, the lean angle may then be used to derive the true bottle dimensions from the measured image data. For example, the true bottle width at the point 1L may be calculated as follows:

$$\text{true width}=\cos(\text{lean angle})\times(1Lx-1Rx)$$

Other true bottle dimensions may be calculated in a similar manner once the lean angle is known.

Correction for Longitudinal Misalignment

It has been found that the position of a bottle such as bottle 52 on conveyor 12 can vary from bottle to bottle. This is because, as bottles are placed onto the conveyor by the blow mold 30, they are not always placed in exactly the same position on the conveyor. Accordingly, the position of a particular bottle can vary both in a transverse direction 114 (in a direction perpendicular to the direction of conveyor movement) and also in a longitudinal direction 116, perpendicular to the transverse direction as shown in FIG. 2.

Referring to FIG. 2, when a bottle 52 is perfectly aligned longitudinally, it will be located at the target site 52 when the strobe 94 is energized. In this case, the bottle 52 will be longitudinally equidistant from the imaging devices 102, 104. When a bottle 52 varies in longitudinal direction 116, however, it will either be downstream (in the direction of the arrow 14) or upstream (in the direction opposite the arrow 14) of the target site 50 when the strobe 94 is energized. If the bottle 52 is downstream, it will be closer to imaging device 104 and further from imaging device 102. Conversely, if the bottle 52 is upstream, it will be closer to imaging device 102 and further from imaging device 104.

When the bottle 52 is closer to one imaging device than the other, the image of the bottle acquired by the closer imaging device will be larger than the image of the bottle acquired by the further imaging device. When this condition is detected by the computer 66, the bottle being imaged is longitudinally misaligned. By measuring the amount of difference in bottle image size, the computer 66 can determine the amount of longitudinal misalignment and correct the image size accordingly.

Correction for Transverse Misalignment

Figure 8:
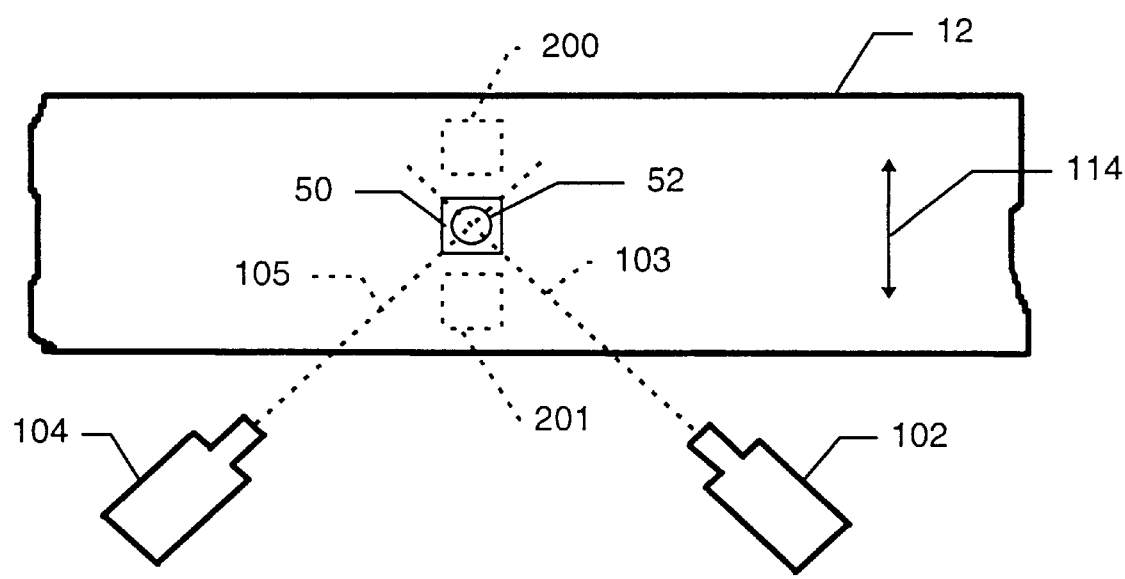
FIG. 8 is a plan view of the imaging device of FIG. 2 schematically illustrating a bottle that is transversely misaligned.

Referring to FIGS. 2 and 8, when a bottle 52 is perfectly aligned in a transverse direction 114, it will be located at the target site 50 when the strobe 94 is energized. When a bottle 52 varies in transverse direction 114, however, it will either be closer to, e.g., position 202, or further from, e.g., position 200, the imaging devices 102, 104, FIG. 8.

FIGS. 9A–11A schematically illustrate the image 194 acquired by the imaging device 104 which includes the bottle image 204. FIGS. 9B–11B illustrate the image 192 acquired by the imaging device 102 which includes the bottle image 202. To determine transverse location, the computer 66 combines the image 192 and the image 194 from the imaging devices 102, 104 into one image 206, FIGS. 9C–11C. If the bottle 52 is perfectly aligned transversely, as shown in FIGS. 2 and 10, the image of the bottle acquired from each imaging device 102, 104 will overlap. The combined image will, thus result in only one bottle image as seen in FIG. 10C.

If, however, the bottle 52 is transversely misaligned closer to the imaging devices 102, 104, e.g. at the position 202, FIG. 8, the bottle image 202 acquired by imaging device 102 will be shifted to the left (since the bottle has shifted to the left in the field of view of imaging device 102). This is best illustrated in FIG. 9B.

In a similar manner, the bottle image 204 acquired by imaging device 104 will be shifted to the right (since the bottle has shifted to the right in the field of view of imaging device 104). This is best illustrated in FIG. 9A.

In such a misaligned configuration, the combined image 206, FIG. 9C will result in the individual bottle images 202, 204 not overlapping. In other words, the edges of the bottle images 202, 204 acquired from imaging devices 102, 104 will not overlap. Specifically, the bottle image 202 acquired by the imaging device 102 will be shifted to the left relative to the bottle image 204 acquired by the imaging device 104 as shown in FIG. 9C.

If the bottle 52 is transversely misaligned further from the imaging devices 102, 104, e.g., at the position 200, FIG. 8, the bottle image 202 acquired by imaging device 102 will be shifted to the right (since the bottle has shifted to the right in the field of view of imaging device 102). This is best illustrated in FIG. 11B.

In a similar manner, the bottle image 204 acquired by imaging device 104 will be shifted to the left (since the bottle has shifted to the left in the field of view of imaging device 104). This is best illustrated in FIG. 11A.

In such a misaligned configuration, the combined image 206, FIG. 11C will result in the individual bottle images 202, 204 not overlapping. In other words, the edges of the bottle images 202, 204 acquired from imaging devices 102, 104 will not overlap. Specifically, the bottle image 202 acquired by the imaging device 102 will be shifted to the right relative to the bottle image 204 acquired by the imaging device 104 as shown in FIG. 11C.

Accordingly, the computer 66 can detect that a transverse misalignment condition exists and can determine in which direction the misalignment occurs. By measuring the distance between the bottle images 202, 204, the computer 66 can also measure the amount of misalignment. Once the amount of misalignment is known, the computer 66 may align the images 202, 204 and adjust the size of the image to compensate for the transverse misalignment. In other words, if the computer 66 detects that the bottle 52 is transversely misaligned further from the imaging devices 102, 104, e.g. at the position 200, the combined bottle image may be enlarged in accordance with the amount of transverse misalignment. In a similar manner, if the computer 66 detects that the bottle 52 is transversely misaligned closer to the imaging devices 102, 104, e.g. at the position 201, the combined bottle image may be reduced in accordance with the amount of transverse misalignment.

Upon initial start-up of the inspection apparatus 64, it may be calibrated by running bottles of known dimensions and characteristics through the inspection apparatus. The computer 64 can then correlate the actual size of these bottles to the size of their images generated by the inspection apparatus 64. The computer 66 may then use this relationship to measure characteristics of unknown bottles as described above.

Although the above methods for correction of orientation and position have been described with respect to bottle inspection, these methods could be used for any inspection task in which the objects being inspected are not uniformly oriented and/or positioned.

Laser Trigger

As described previously, the computer 66, FIG. 1, may detect pulses from the I.S. machine in order to determine when to energize the strobe light 94, 138 and 140, FIGS. 2, 3 and 12, and to correlate each bottle being imaged to the mold which created the bottle. As an alternative to using the I.S. machine pulses to determine when to energize the strobe light, a laser trigger device may, alternatively, be used as will now be described in detail.

Figure 15:
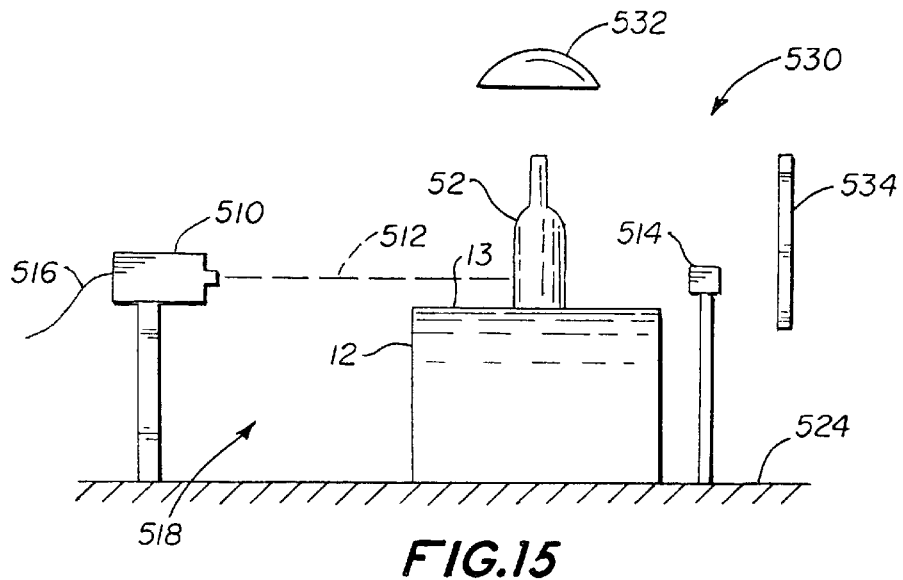
FIG. 15 is a cross-sectional elevation view of a bottle conveyor and an associated laser triggering device.

Referring to FIG. 15, a laser device 510 may be located adjacent the conveyor 12 in the vicinity of the image generating device housings 100, 120 or 300 and 350. It is noted that, for the sake of clarity, the housing(s) has been omitted from FIG. 15. The laser device 510 may be located so as to direct a laser beam 512 across the top of the conveyor 12 and onto a reflector 514 located on the opposite side of the conveyor 12. The height of the laser device 510 is set so that the laser beam 512 will be interrupted by a bottle 52 being transported by the conveyor 12 when the bottle passes between the laser device 510 and the reflector 514. Both the laser device 510 and the reflector 514 may be mounted to the production facility floor 524 in any conventional manner.

When no bottle is located between the laser device 510 and the reflector 514, the laser beam 512 is reflected by the reflector 514 back to a detector located on the laser device 510. The detector is, thus, able to detect the reflected laser beam, indicating that no bottle is present in the target area. When a bottle passes between the laser device 510 and the reflector 514, however, the laser beam 512 is blocked and the detector located on the laser device 510 is not able to detect the reflected laser beam, thus indicating that a bottle is located within the target area.

The laser device 510 may include a data connection 516 which connects with the computer 66 in a conventional manner. In this fashion, the laser device is able to signal the computer 66 when a bottle is within the target area and, thus, cause the strobe light or lights to fire, enabling an image of the bottle to be acquired in a manner as previously described.

It has been found that the laser triggering arrangement described above more accurately indicates when a bottle has entered the target area than does the I.S. machine pulse detection method previously described. It is noted that, even when using the laser triggering method, the I.S. machine pulses may still be monitored in order to provide correlation between the particular bottle being imaged and its mold of origin in the I.S. machine.

Laser device 510 may be a conventional laser triggering device, such as the type commercially available from The Allen Bradley Company of Milwaukee, Wis. and sold as Model No. SX 12L.

One problem with the laser triggering arrangement described above is that it is sometimes necessary for human operators to enter the area 518 between the conveyor 12 and the laser device 510. Such entry into the area 518 often results in the human operator's body blocking the laser beam 512. This, in turn, indicates to the detector in the laser device 510 that a bottle is in the target area and, thus, results in an erroneous signal being sent to the computer 66 via the data connection 516.

Figure 16:
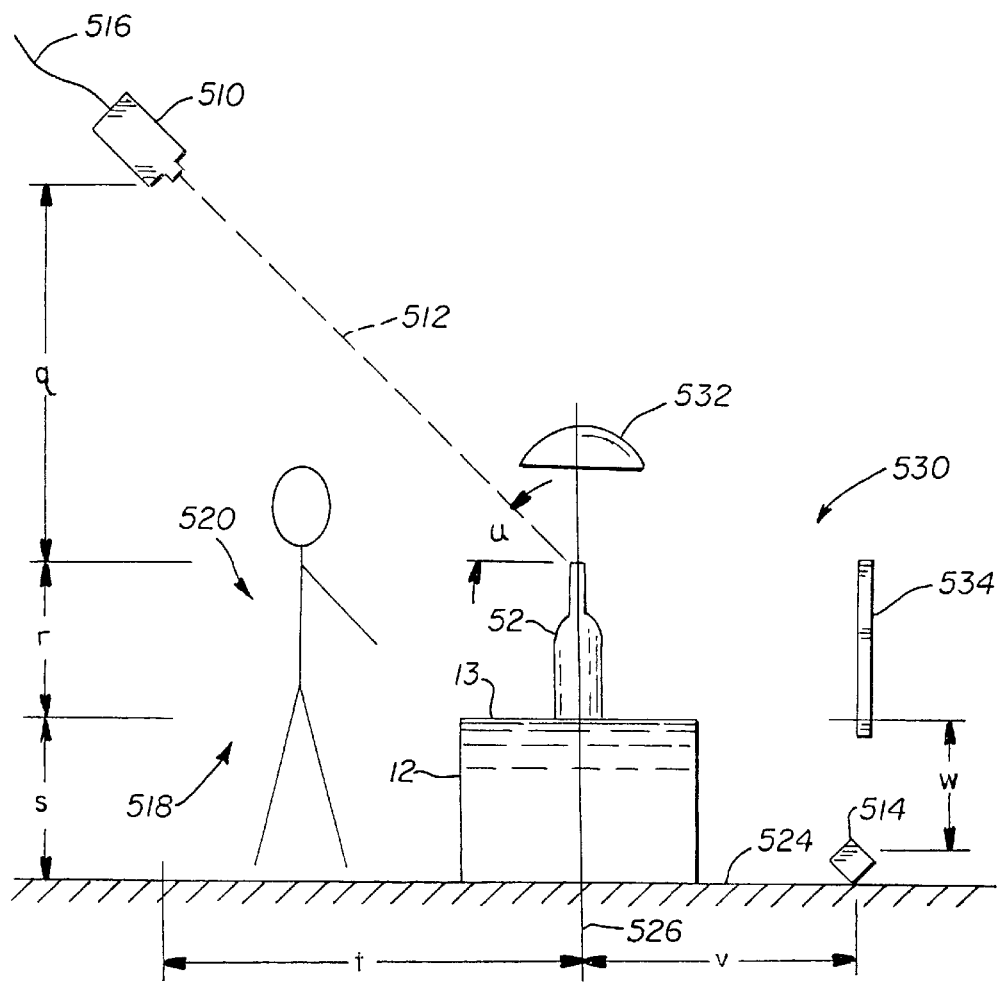
FIG. 16 is a cross-sectional elevation view of a bottle conveyor and another embodiment of a laser triggering device.

FIG. 16 illustrates an improved laser trigger arrangement in which a human operator 520 standing in the area 518 will not interfere with the laser beam 512. As can be seen from FIG. 16, the laser device 510 may be mounted at an elevated location such that the laser beam 512 will pass above an operator 520 standing near the conveyor 12 in the area 518 and the operator 520 will not cause interference with the laser beam 512. To achieve this result, the laser device 510 is located and aimed such that the laser beam 512 forms a relatively steep angle "u" with respect to the plane of the upper surface 13 of the conveyor 12. The laser device 510 may be located a vertical distance "q" of about 20.0 feet above the upper neck area 22 of the bottle 52. With an exemplary bottle height "r" of about 9.0 inches, the laser device 510 will be located approximately 20 feet, 9 inches ("q" plus "r") above the upper surface 13 of the conveyor 12. With the upper surface 13 of the conveyor 12 located an exemplary distance "s" of about 3.0 feet above the floor 524, the laser device 510 will be located about 23 feet, 9 inches ("q" plus "r" plus "s") above the floor 524. The laser device 510 may be located a horizontal distance "t" of about 15.0 feet from the centerline 526 of the conveyor. With the exemplary dimensions set forth above, the angle "u" formed between the laser beam 512 and the conveyor upper surface 13 will be about 60 degrees. The laser device may, for example, be mounted either directly or indirectly to the ceiling of the production facility.

As previously noted, the relatively steep angle "u" allows the laser beam 512 to intersect the upper portion 522 of a bottle in the target area while avoiding interference by a human operator 520 standing near the conveyor 12 adjacent the target area. The steep angle "u" also results in the reflector 514 being located below the plane of the conveyor upper surface 13. This is advantageous since, located below the conveyor upper surface 13 in this manner, the reflector 514 is exposed to much less heat than it is when located above the conveyor upper surface 13 as shown in FIG. 15. Preferably, the angle "u" should be from about 60 to about 70 degrees.

The reflector 514 may be located a horizontal distance "v" of about 10.0 inches from the conveyor centerline 526 and a vertical distance "w" of about 14.0 inches below the conveyor upper surface 13.

Electronically Shuttered Imaging Device

The imaging apparatus and methods set forth previously have been described in conjunction with a strobe light or lights. Such strobe lights may be used in a conventional manner to "freeze" the moving target bottle and fix an image thereof on the applicable image generating device. Although strobe lights generally function well for this purpose, there are some disadvantages associated with the use of strobe lights. For example, flashing strobe lights are often found to be irritating to human operators in the area. Strobe lights create "electrical noise" which may interfere with computers and other electronic systems, such as the computer 66 previously described. Strobe lights also take up space near the bottle production line which might otherwise be used for other purposes. Finally, strobe lights represent relatively expensive, high maintenance items.

Strobe lights may be eliminated, and the disadvantages discussed above avoided, by utilizing an electronically shuttered imaging device. Such devices are commonly used to image moving objects. An electronically shuttered imaging device may be a CCD device, similar to the imaging devices 102, 104 previously described. An electronically shuttered imaging device, however, also includes electronic circuitry which enables the device to "freeze" an image of a moving target without using a strobe light.

Accordingly, in all of the apparatus and methods previously described, electronically shuttered imaging devices may be used in place of the imaging devices 102 and 104 and the previously described strobe lights may be eliminated. The electronically shuttered imaging device used may be of the type commercially available from Hitachi Benshi Ltd. of Tokyo, Japan and sold as Model No. KPf1. The electronically shuttered imaging devices may be triggered either by pulses from the I.S. machine or by the a laser trigger device, in a manner as previously described. In all other aspects, the electronically shuttered imaging device may operate in a similar manner to that previously described with respect to the imaging devices 102, 104.

When using an electronically shuttered imaging device, although no strobe light is required, the bottle 52 being imaged must still be adequately illuminated. Although any conventional illumination source may generally be used, one specific and preferred type of illumination source will now be described in detail with reference to FIGS. 15 and 16.

FIGS. 15 and 16 illustrate a conventional bottle visual inspection station 530 of the type that is commonly used in bottle manufacturing plants. The station 530 generally includes a light source 532 which may be, for example, an AC powered halogen light source, and a reflector board 534. Light from the light source 532 illuminates the bottles as they pass beneath the light source. This light is then reflected off of the bottles, allowing an operator 520 to visually inspect the bottles. Further, light from the light source is erflected by the reflector board 534 and passes through the walls of the bottles, allowing the operator 520 to view light which is transmitted through the bottles.

It has been found that the existing halogen light source 532, described above, adequately illuminates the bottles, allowing the electronically shuttered image generating devices to acquire images of the bottles in a manner as previously described. This is advantageous since use of the existing light source eliminates the need to provide separate or additional light sources for the imaging system. It has been found, however, that the intensity of light provided by AC light sources, such as the halogen light source described above, tends to fluctuate over time. This fluctuation is believed to be due to the sinusoidal characteristic of the AC power supply. Although such fluctuation generally occurs at too high a frequency to permit detection by the human eye, it may readily be detected by a high-speed imaging device, such as the electronically shuttered imaging devices described above.

In order to reduce the effect on acquired images of the fluctuations described above, it has been found to be beneficial to operate the halogen light source at a wattage lower than its rated wattage. In one example, a 500 watt halogen bulb located in the light source 532 may be operated at about 300 watts. In order to accomplish this wattage reduction, the voltage supplied to the halogen bulb may be reduced accordingly. It has been found that operating the light source in this manner significantly reduces the effect of AC power induced light fluctuations. Accordingly, operating a conventional AC light source in this manner allows an existing AC-powered halogen light source to be used to acquire high quality images with an electronically shuttered imaging device.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. Apparatus for measuring at least one unknown characteristic of objects being conveyed along an object pathway on a conveyor comprising:
   (a) an enclosure located adjacent said conveyor;
   (b) said enclosure defining an enclosure interior located within said enclosure and an enclosure exterior located outside of said enclosure;
   (c) an opening in said enclosure, said opening extending between said enclosure exterior and said enclosure interior;
   (d) a sleeve member having a first end and a second end, said sleeve member first end located proximate said enclosure opening;
   (e) an image generating device located in said enclosure interior and aimed through said sleeve member at a location within said object pathway;
   (f) said sleeve member second end located proximate said image generating device.

2. The apparatus of claim 1 wherein said sleeve member first end is attached to said enclosure.

3. The apparatus of claim 2 wherein said sleeve member comprises an annular cylinder.

4. The apparatus of claim 3 wherein said sleeve member is press-fit within said opening.

5. The apparatus of claim 1 wherein said enclosure interior is pressurized to a pressure higher than that of said enclosure exterior.

6. The apparatus of claim 5 wherein a cooling fluid supply line is connected to said enclosure.

7. The apparatus of claim 1 wherein said image generating device is slidingly mounted to said enclosure.

8. The apparatus of claim 1 further including a slide mount assembly located between said image generating device and said enclosure.

9. The apparatus of claim 1 wherein said enclosure is a parallelepiped-shaped housing having a length substantially equal to 12 inches, a width substantially equal to 3 inches, and a height substantially equal to 6 inches.

10. The apparatus of claim 1 further comprising:
    a. a remote computer; and
    b. a data connection connected to said image generating device and to said remote computer.

11. The apparatus of claim 1 wherein said image generating device includes a lens assembly.

12. The apparatus of claim 11 wherein said sleeve member second end is located proximate said image generating device lens assembly.

13. The apparatus of claim 12 wherein said lens assembly includes a substantially annular housing and a lens located within said substantially annular housing.

14. The apparatus of claim 13 wherein said image generating device further includes a photoelectric device operatively associated with said lens.

15. Apparatus for measuring at least one unknown characteristic of objects being conveyed along an object pathway on a conveyor comprising:
    (a) a first enclosure located adjacent said conveyor;
    (b) a second enclosure located adjacent said conveyor;
    (c) each of said first and second enclosures including:
        (i) an enclosure interior located within said enclosure and an enclosure exterior located outside of said enclosure;
        (ii) an opening in said enclosure, said opening extending between said enclosure exterior and said enclosure interior;
        (iii) a sleeve member having a first end and a second end, said sleeve member first end located proximate said enclosure opening;
        (iv) an image generating device located in said enclosure interior and aimed through said sleeve member at a location within said object pathway; and
        (v) said sleeve member second end located proximate said image generating device.

16. The apparatus of claim 15 further comprising:
    (a) a remote computer; and
    (b) a data connection connected to each of the first enclosure and second enclosure image generating devices and to said remote computer.

17. The apparatus of claim 15 wherein said image generating device includes a lens assembly.

18. The apparatus of claim 17 wherein said sleeve member second end is located proximate said image generating device lens assembly.

19. The apparatus of claim 18 wherein said lens assembly includes a substantially annular housing and a lens located within said substantially annular housing.

20. The apparatus of claim 19 wherein said image generating device further includes a photoelectric device operatively associated with said lens.

* * * * *